US010631899B2

(12) United States Patent
Friedrich et al.

(10) Patent No.: US 10,631,899 B2
(45) Date of Patent: *Apr. 28, 2020

(54) FLEXIBLE SPINE STABILIZATION SYSTEM

(71) Applicant: GLOBUS MEDICAL, INC., Audubon, PA (US)

(72) Inventors: Adam Friedrich, Cinnaminson, NJ (US); Andrew Iott, Newtown Square, PA (US); Edward Karpowicz, Sewell, NJ (US); Anand Balasubramanian, Collegeville, PA (US); Edward Dwyer, Lehighton, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/109,831

(22) Filed: Aug. 23, 2018

(65) Prior Publication Data

US 2019/0000511 A1 Jan. 3, 2019

Related U.S. Application Data

(63) Continuation of application No. 14/876,883, filed on Oct. 7, 2015, now Pat. No. 10,085,772, which is a continuation-in-part of application No. 13/894,903, filed on May 15, 2013, now Pat. No. 9,339,297, which is a continuation of application No. 12/112,096, filed on Apr. 30, 2008, now Pat. No. 8,465,526.

(60) Provisional application No. 60/914,993, filed on Apr. 30, 2007.

(51) Int. Cl.
*A61B 17/70* (2006.01)

(52) U.S. Cl.
CPC ...... *A61B 17/7031* (2013.01); *A61B 17/7001* (2013.01); *A61B 17/702* (2013.01); *A61B 17/7007* (2013.01); *A61B 17/7008* (2013.01)

(58) Field of Classification Search
CPC ........................................ A61B 17/7019–7031
See application file for complete search history.

(56) References Cited

U.S. PATENT DOCUMENTS

| | | | |
|---|---|---|---|
| 10,085,772 B2 * | 10/2018 | Friedrich ........... | A61B 17/7031 |
| 2006/0129149 A1 * | 6/2006 | Iott ................... | A61B 17/7032 |
| | | | 606/278 |
| 2006/0247779 A1 * | 11/2006 | Gordon ............. | A61B 17/7005 |
| | | | 623/17.15 |

(Continued)

*Primary Examiner* — Nicholas J Plionis

(57) ABSTRACT

A system for flexibly stabilizing a vertebral motion segment by connecting a first vertebra and a second vertebra is disclosed. The system includes an elongate connection element with end portions interconnected by a flexible coupling member. The system includes first and second attachment portions for connecting the connection element to the vertebrae. A first resilient member is positioned between the first end portion and the first attachment portion, and a second resilient member is positioned between the first attachment portion and the second attachment portion. The system is designed such that the second resilient member is compressed when the first and second attachment portions move towards each other, and the first resilient member is compressed when the first and second attachment portions extend away from each other.

19 Claims, 32 Drawing Sheets

(56) References Cited

U.S. PATENT DOCUMENTS

| | | | |
|---|---|---|---|
| 2007/0055244 A1* | 3/2007 | Jackson | A61B 17/7028 606/86 A |
| 2007/0093817 A1* | 4/2007 | Barrus | A61B 17/7032 606/264 |
| 2007/0276380 A1* | 11/2007 | Jahng | A61B 17/1757 606/86 A |
| 2008/0234737 A1* | 9/2008 | Boschert | A61B 17/7031 606/254 |
| 2009/0005817 A1* | 1/2009 | Friedrich | A61B 17/7007 606/246 |
| 2009/0105756 A1* | 4/2009 | Richelsoph | A61B 17/7032 606/246 |
| 2009/0234388 A1* | 9/2009 | Patterson | A61B 17/702 606/246 |

* cited by examiner

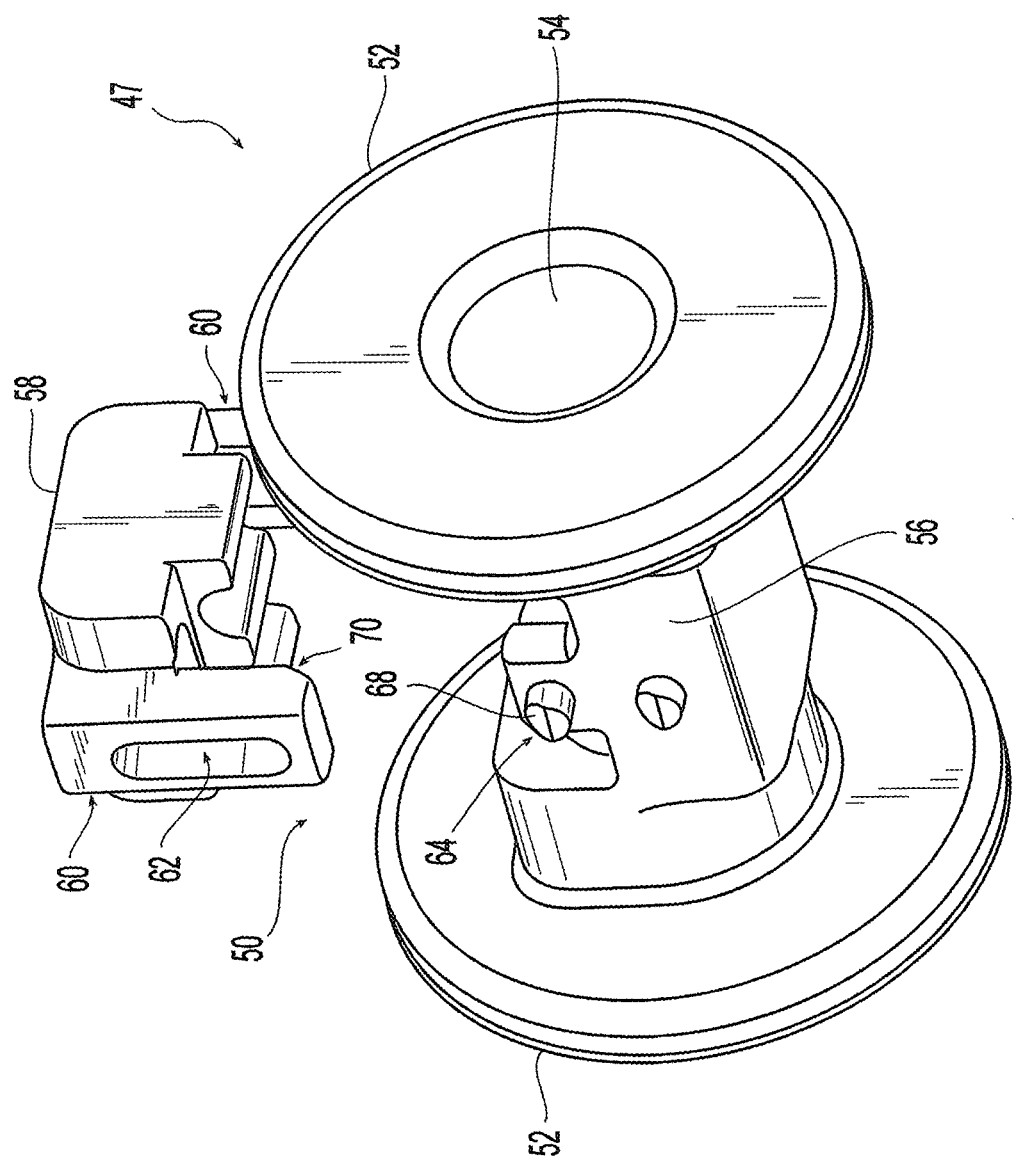

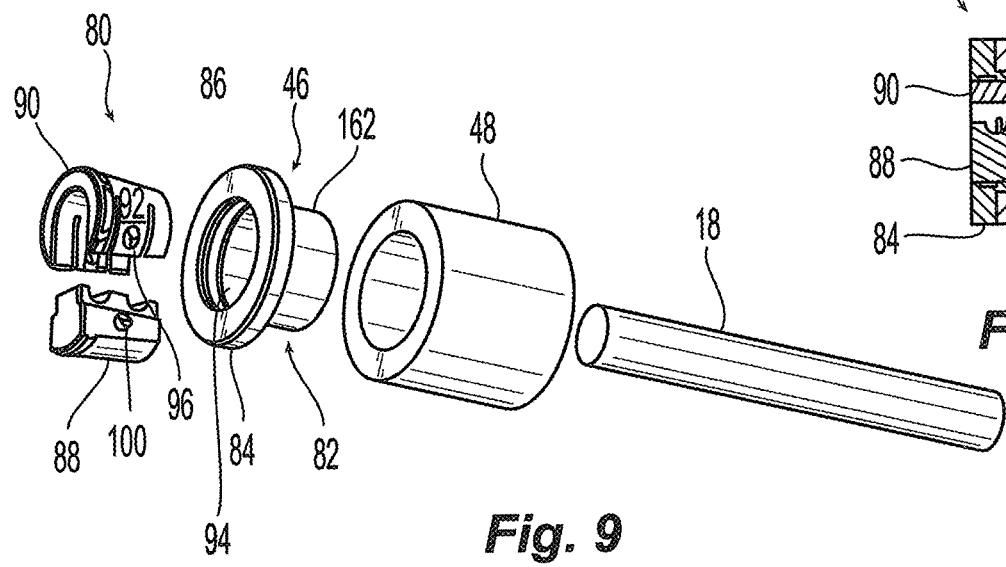
Fig. 9
Fig. 12
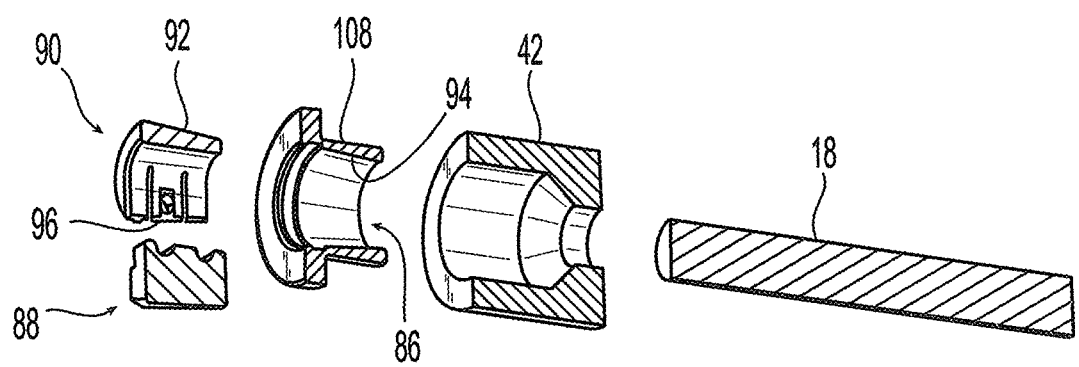
Fig. 10

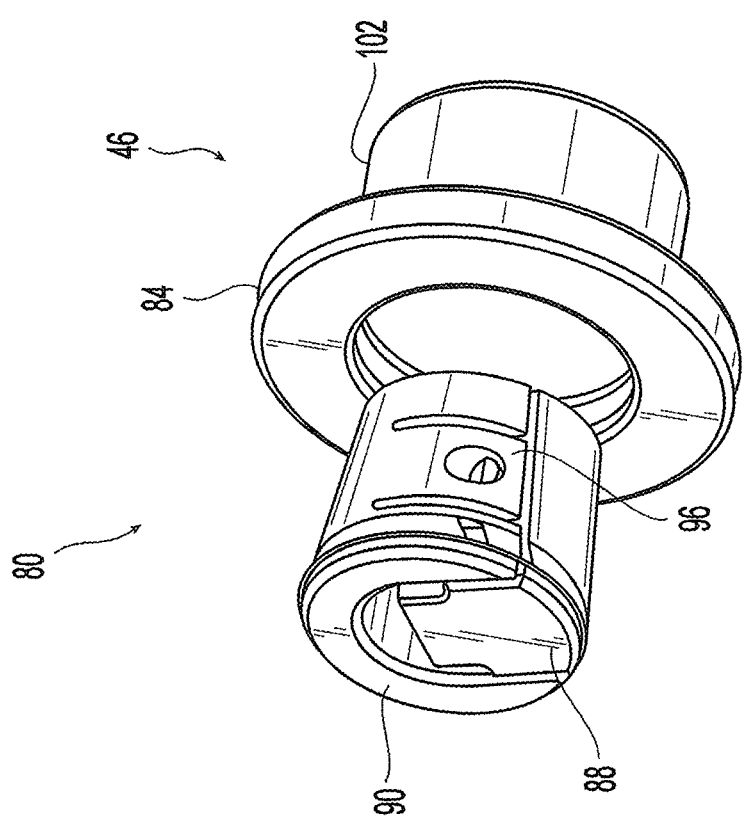

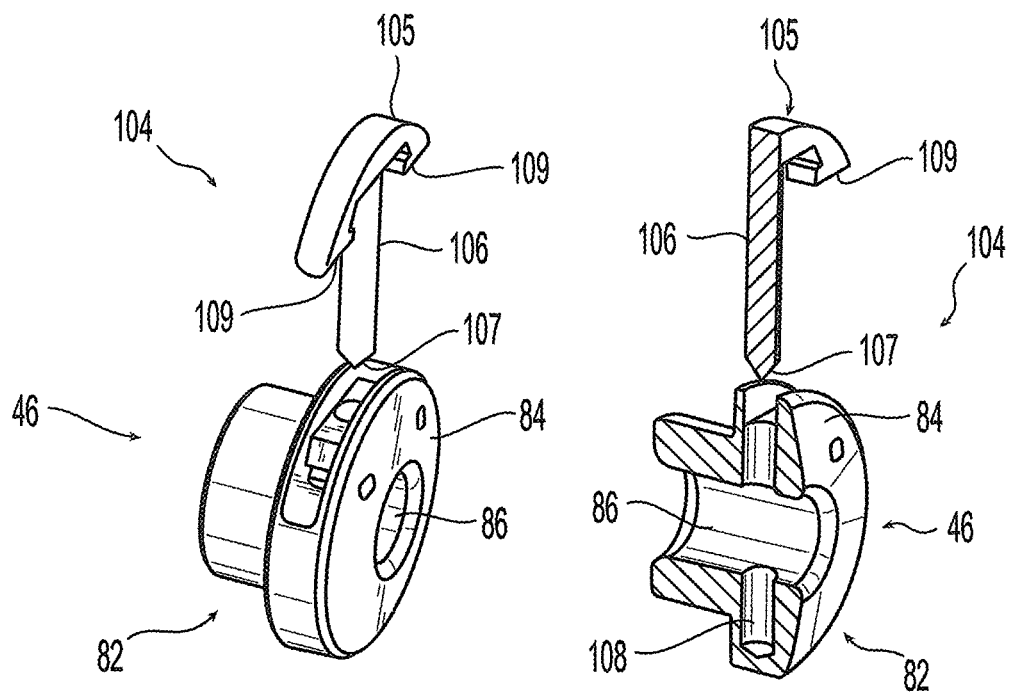
*Fig. 12A*  *Fig. 12B*
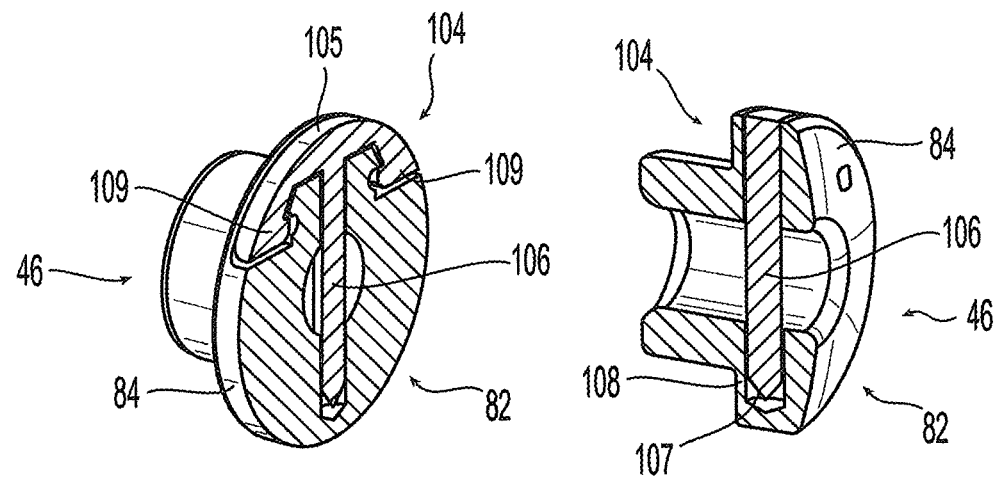
*Fig. 12C*  *Fig. 12D*

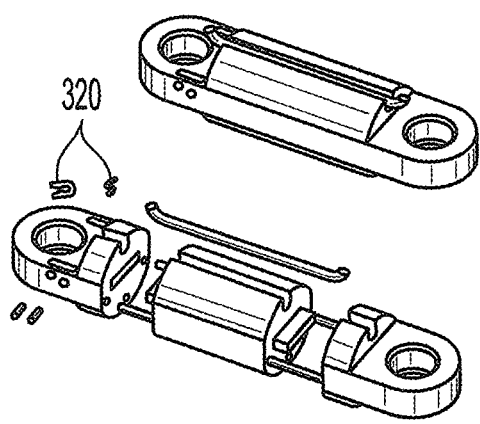
Fig. 31
Fig. 32
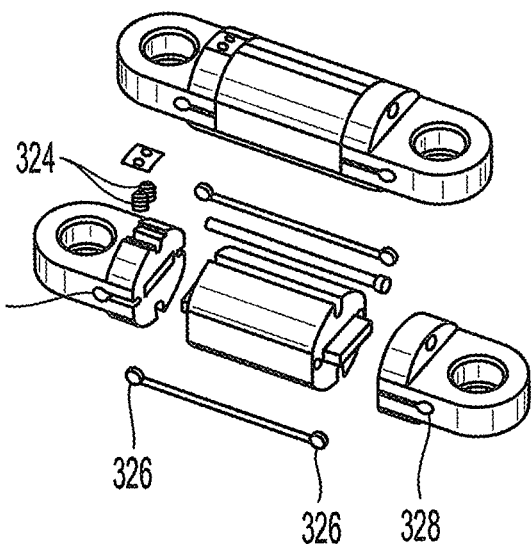
Fig. 33
Fig. 34

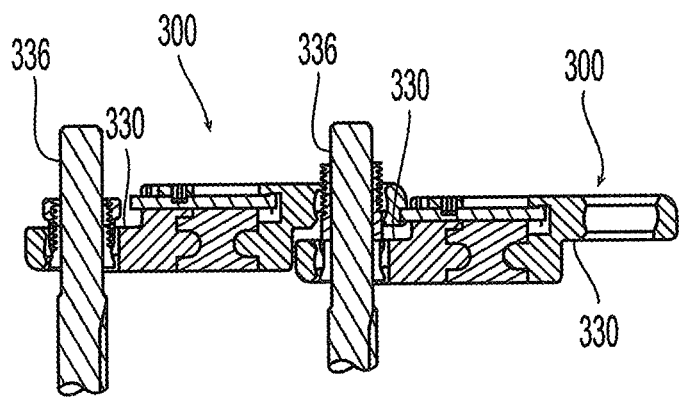
Fig. 35
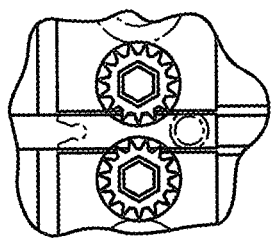
Fig. 36A
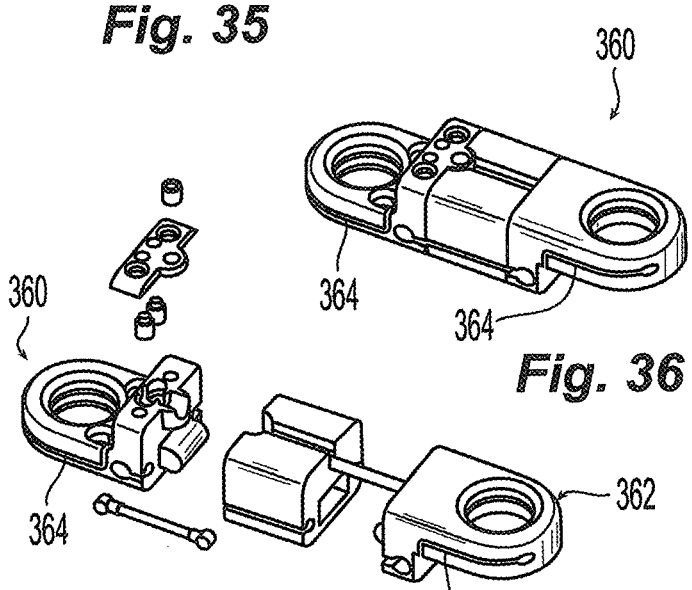
Fig. 36
Fig. 37
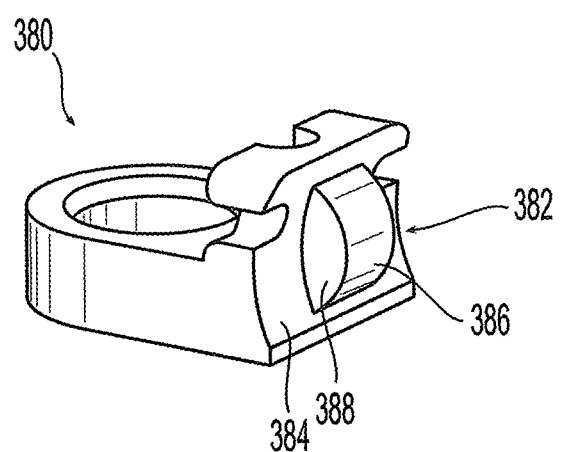
Fig. 38

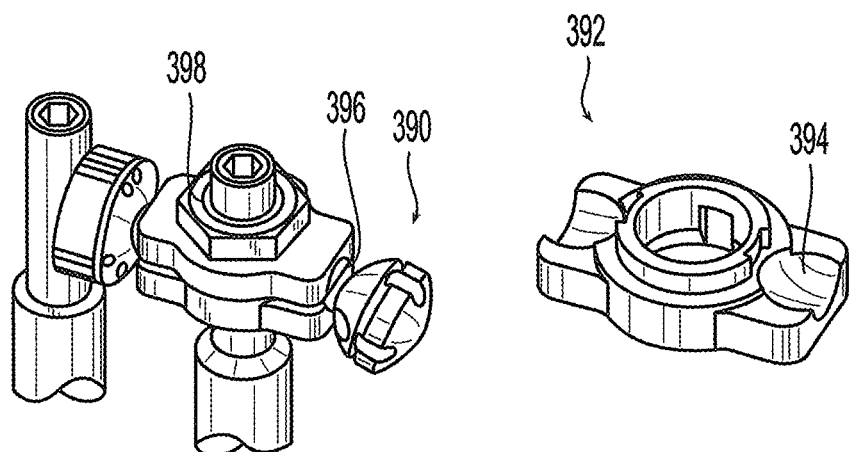
Fig. 39
Fig. 40
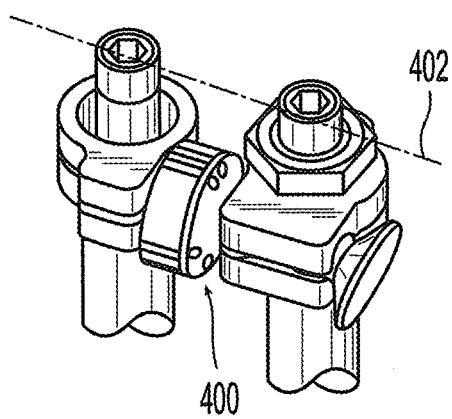
Fig. 41

FLEXIBLE SPINE STABILIZATION SYSTEM

CROSS-REFERENCE TO RELATED APPLICATIONS

This application is a continuation of U.S. patent application Ser. No. 14/876,883 filed on Oct. 7, 2015 which is a continuation-in-part application of U.S. patent application Ser. No. 13/894,903, which is a continuation of U.S. patent application Ser. No. 12/112,096 filed on Apr. 30, 2008, now issued as U.S. Pat. No. 8,465,526, which claims priority to U.S. Provisional Application Ser. No. 60/914,993 filed on Apr. 30, 2007, which is incorporated herein by reference in its entirety.

FIELD OF THE INVENTION

The present disclosure generally relates to flexible stabilization systems for spinal motion segment units. In particular, certain embodiments are directed to a soft stabilization system including at least two bone fasteners and a flexible portion conformable to the natural spinal movement.

BACKGROUND OF THE INVENTION

The spine includes a series of joints routinely called motion segment units, which is the smallest component of the spine that exhibits kinematic behavior characteristic of the entire spine. The motion segment unit is capable of flexion, extension, lateral bending and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. Thus, rigid stabilization of one or more motion segment units may be an important element of a surgical procedure in certain cases (i.e., injuries, deformities, tumors, etc.), whereas it is a complementary element in others (i.e., fusion performed due to degeneration). The purpose of rigid stabilization is the immobilization of a motion segment unit.

As mentioned above, current surgical techniques typically involve fusing one or more unstable motion segment units and possibly, the removal of ligaments, bone, disc, or combinations thereof included in the unstable motion segment unit or units prior to fusing. There are several disadvantages to fusion, however. For example, the fusing process results in a permanent or rigid internal fixation of all or part of the intervertebral joints and usually involves metallic rods, plates, and the like for stabilization. In all cases, the systems are intended to rigidly immobilize the motion segment unit to promote fusion within that motion segment unit.

In addition to a loss of mobility, fusion also causes the mobility of the motion segment to be transferred to other motion segments of the spine. The added stresses transferred to motion segments neighboring or nearby the fused segment can cause or accelerate degeneration of those segments. One other disadvantage to fusion is that it is an irreversible procedure. In addition, it is believed that fusion of a motion segment has a clinical success of approximately 70 percent, and often does not alleviate pain experienced by the patient.

Thus, while such fusion systems have been used since the early 1960's, the intentionally rigid designs have often caused stress concentrations and have directly and indirectly contributed to the degeneration of the joints above and below the fusion site (as well as at the fusion site itself). In addition, rigid, linear bar-like elements eliminate the function of the motion segment unit. Finally, removal of portions of the motion segment unit reduces the amount of support available for the affected motion segment unit.

Fusion procedures can be improved by modifying the load sharing characteristics of the treated spine. Thus, it would be desirable to allow more of a physiologic loading between pedicular fixation and anterior column support. It would also be desirable to have a device that precludes or at least delays the need for fusion for all but the most advanced degeneration of a motion segment, particularly if such a device would allow close to normal motion and pain relief.

Thus, a need exists in the art for a soft spine stabilization system that replicates the physiologic response of a healthy motion segment.

SUMMARY OF THE INVENTION

According to one aspect, a flexible spinal stabilization system that can provide load sharing either as an enhancement to a fusion device or as a motion-preserving non-fusion device is provided.

According to another aspect, a flexible prosthesis for intervertebral or intersegmental stabilization designed to load share with a graft in the anterior column that allows for graft resorption while ensuring compressive loading on the graft for fusion procedures in the spine is provided.

Another embodiment is directed towards a device for intervertebral or intersegmental stabilization designed to ensure proper alignment and motion between vertebrae of the spinal column that helps partially unload the discs and facet joints to give pain relief.

According to another aspect, a flexible connection element may be used to as part of various components of a spine stabilization system. For instance, the flexible connection element may form all or part of one longitudinal stabilization members. In another aspect, the flexible connection element may also form at least part of a transconnector. Depending on what component of the spine stabilization system uses the invention, fasteners may also be connected to the component. For instance, in one embodiment the flexible connection element is connected to bone fasteners, such as pedicle screws or the like.

BRIEF DESCRIPTION OF THE DRAWINGS

FIG. 1A is a perspective view of a portion of a flexible connection element according to the invention;

FIG. 6 is an exploded view of one embodiment of an end portion of the flexible connection element of FIG. 5;

FIGS. 9-10 are exploded views of an embodiment of another end portion of the flexible connection element of FIG. 5;

FIG. 11 is a partial assembled view of the end portion of FIGS. 9-10 shown in a second position;

FIG. 12 is a cross-sectional view of the end portion of FIGS. 9-11 shown in a second position;

FIGS. 12A-12B are exploded perspective and exploded cross-sectional views, respectively, of an embodiment of another end portion of the flexible connection element of FIG. 5;

FIGS. 12C-12D are assembled cross-sectional views of the embodiment of FIGS. 12A-12B;

FIGS. 31-32 are perspective and exploded views, respectively, of another embodiment of a flexible connection element;

FIGS. 33-34 are perspective and exploded views, respectively, of another embodiment of a flexible connection element;

FIG. 35 is an cross-sectional view of another embodiment of a flexible connection element;

FIGS. 36-37 are perspective and exploded views, respectively, of another embodiment of a flexible connection element;

FIG. 38 is a perspective view of another embodiment of an end portion according to the invention;

FIGS. 39-40 are perspective and partial exploded views, respectively, of another embodiment of a flexible connection element;

FIG. 41 is a perspective view of another embodiment of a flexible connection element;

BRIEF DESCRIPTION OF THE ILLUSTRATED EMBODIMENTS

Figure 1:
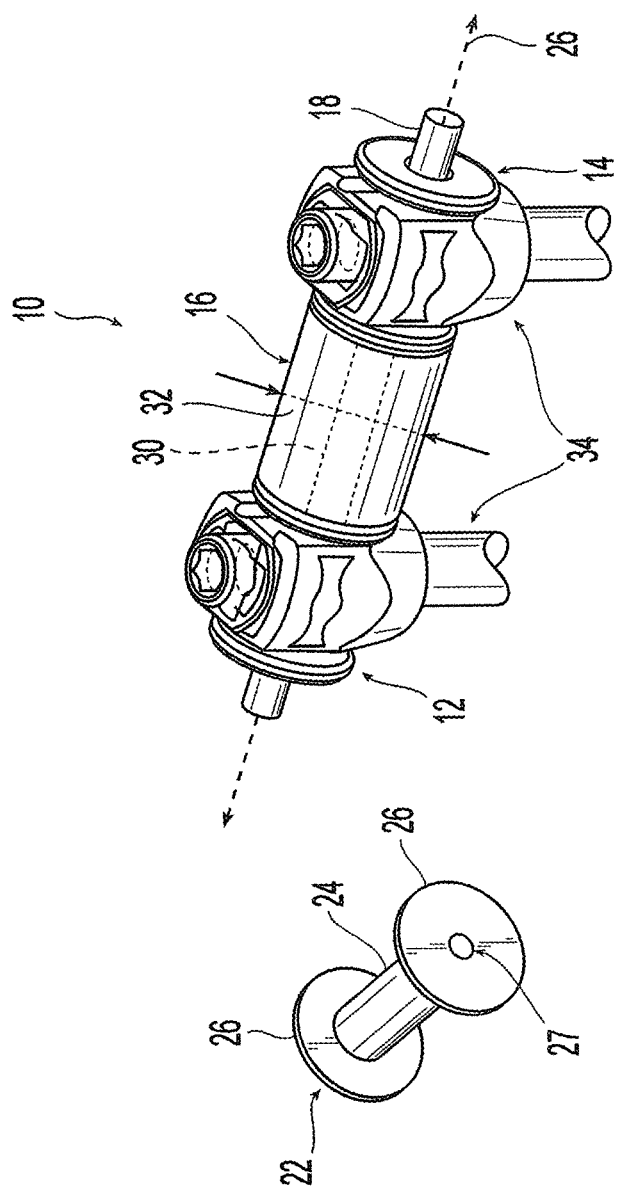
FIG. 1 is a perspective view of one embodiment of a flexible connection element according to the invention.

Embodiments of the disclosure are generally directed to flexible stabilization systems for use with the anterior, antero-lateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

One embodiment of a spine stabilization system described herein includes at least two bone fasteners and at least one flexible connection element extending at least partially between the bone fasteners. In general, the flexible connection element may advantageously provide desirable properties for bending or twisting that allows the system to accommodate natural spine movement. According to some embodiments, the flexible connection element approximates or resembles a relatively circular cross-section tube or rod. In alternate embodiments, a flexible connection element may have other shapes as well. For instance the flexible connection element may have a cross-section that approximates or resembles a circle, an oval, an ellipse, or angular geometric shapes such as triangles, squares, rectangles, trapezoids, or the like. In many embodiments, the flexible connection element may be made from more than one component and the flexible connection element may have complex and varied cross-sections along its length. It should be understood that in these examples the different types of flexible connection elements described herein may be replaced or interchanged with a flexible connection element having different shapes or configurations, including the many variations described herein.

Embodiments of the present disclosure may also be used as a cross-brace or transconnector in communication with two rods along a portion of the length of the spine. It is well known that the strength and stability of a dual rod assembly can be increased by coupling the two rods with a transconnector that extends across the spine in a direction that is generally perpendicular to the longitudinal axes of the rods. When used as a transconnector, the disclosed embodiments may include a first fastener connecting the transconnector to a first rod and a second fastener connecting the transconnector to a second rod. Alternatively, the transconnector may be connected to one or more bone fasteners associated with a rod. Examples of transconnector designs that may be improved by the present disclosure are described in U.S. Pat. No. 5,743,911 to Cotrel, U.S. Pat. No. 5,651,789 to Cotrel, U.S. Pat. No. 6,139,548 to Errico, U.S. Pat. No. 6,306,137 to Troxell, U.S. Pat. No. 5,947,966 to Drewry, U.S. Pat. No. 5,624,442 to Mellinger, and U.S. Pat. No. 6,524,310 to Lombardo, all of which are incorporated herein in their entirety.

As explained in greater detail below, the flexible connection element can be configured in many different ways. For instance, the flexible connection element may be a relatively straight connection element, such as shown in FIG. 1. Alternatively, the flexible connection element may have a curved shape that corresponds approximately to the natural curvature of the portion of the spine that it supports. In each embodiment, the flexible connection element may be made of one or more components that are configured to allow the element to flex, bend, or twist.

The Flexible Connection Element

Embodiments of the flexible connection element generally provide stability, strength, flexibility, and resistance without the traditional rigidity of prior systems. While the flexible connection element may be designed in a variety of ways according to the invention, the types of design may differ depending on the final implementation of the system, i.e., lateral, posterior, etc. In a posterior application, for example, the flexible connection element may include a straight or curved profile along its length.

Referring to FIG. 1, one embodiment of a flexible connection element 10 is shown. Connection element 10 generally comprises first and second end members or portions 12, 14 and an intermediate portion or spacer 16 disposed therebetween. End portions 12, 14 and spacer 16 are disposed about a coupling member, such as a tether, cable, or cord 18 and extend along a longitudinal axis 20. End portions 12, 14 are configured and dimensioned to be accepted and retained by a bone fastener or anchor such as a pedicle screw 34 or laminar hook. In general, end portions 12, 14 are made from a generally rigid material such as, for example, titanium or any other known biocompatible metal or rigid material. Intermediate portion 16 may be a flexible or resiliently deformable member that provides force absorbing effect in transmitting spinal column loads between the anchors to which flexible connection element 10 is engaged. Intermediate portion 16 may also permit relative movement between first and second end portions 12, 14.

Figure 2:
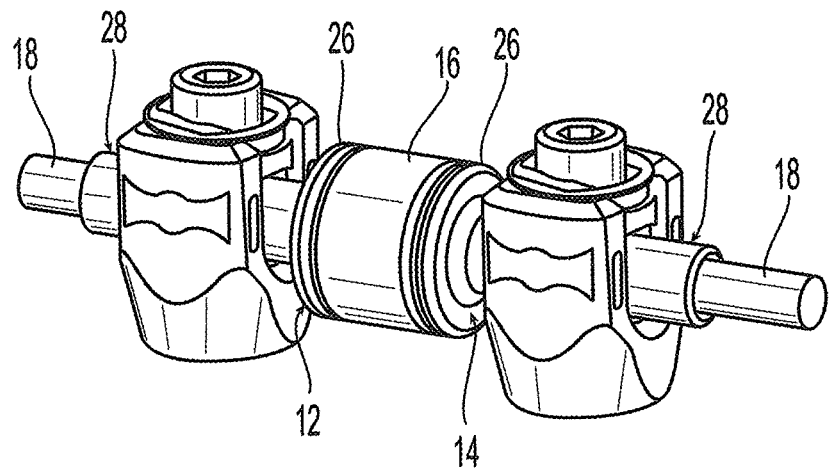
FIG. 2 is a perspective view of another embodiment of a flexible connection element.
Figure 3:
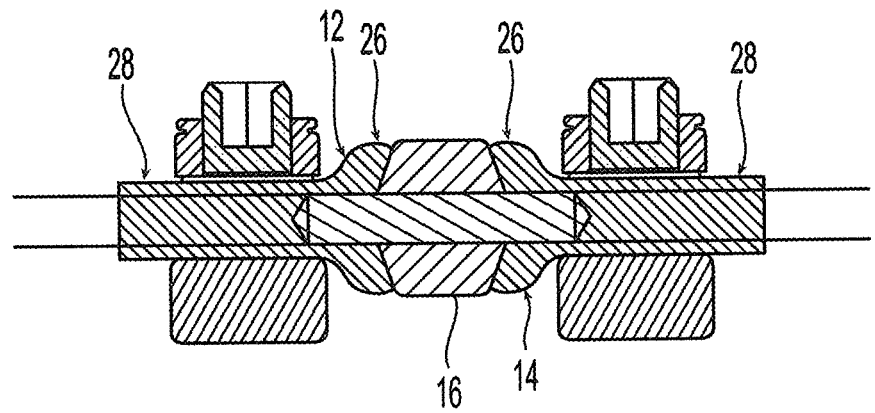
FIG. 3 is a cross-sectional view of another embodiment of a flexible connection element.

Various embodiments of flexible connection element 10 contemplate various alternative configurations of end portions 12, 14 intermediate portions 16, and/or techniques for securing end portions 12, 14. As best seen in FIG. 1A, end portions 12, 14 may be in the form of spools and may have a generally barbell shaped body 22 with a middle body portion 24 extending between end plates or flanges 26. The spacing between flanges 26 and the size of middle portion 24 may be dimensioned to fit within preexisting pedicle screw systems, such as those having an upright yoke or tulip-like receptacle. For instance, middle portion 24 may have a cylindrical shape and may be received in a pedicle screw similar to a cylindrical rod in other known stabilization systems. A channel or opening 27 may extend at least partially through body 22 for accommodating a coupling element or cord 18. In alternate embodiments, such as those shown in FIGS. 2 and 3, spool members 12, 14 may have one end plate or flange 26 configured to engage intermediate portion 16 and the opposing end 28 may be cylindrical or rod shaped and may not have a flange. Cord 18 may extend entirely through the spools, as shown in FIGS. 1 and 2, or cord 18 may extend only partially within spools 12, 14, as shown in FIG. 3.

According to the embodiment of FIG. 1, end portions or spools 12, 14 may be affixed to cord 18 and intermediate portion 16 may be slidable or moveable with respect to cord 18. Any known means or method may be used to secure or affix cord 18 to spools 12, 14. According to one variation, a mechanical clamping member such as a set screw may be used to affix spools 12, 14 to cord 18. In the embodiment of FIG. 3, cord 18 may be crimped, glued, or otherwise secured to spools 12, 14. In alternate embodiments discussed in more detail below, one or more spools 12, 14 may be slidable or moveable about cord 18.

Intermediate portion or spacer 16 may be made from a flexible, soft, and/or elastically resilient or deformable biocompatible material such as for example, a biocompatible elastomer, silicone, polyurethane or polycarbonate urethane or any other known similar material. The intermediate portion may vary somewhat in shape, size, composition, and physical properties, depending upon the particular joint or level for which the implant is intended. The shape of the body of the intermediate portion should complement that of the adjacent end portion(s) or plates to which it engages to allow for a range of translational, flexural, extensional, and rotational motion, and lateral bending appropriate to the particular joint being replaced. The thickness and physical properties of the intermediate portion should provide for the desired degree of elasticity or damping. However, the intermediate portion should be sufficiently stiff to effectively cooperate with the end portions to limit motion beyond the allowable range. Polyurethane-containing elastomeric copolymers, such as polycarbonate-polyurethane elastomeric copolymers and polyether-polyurethane elastomeric copolymers, generally having durometer ranging from about shore 80A to about shore 100A and between about shore 30D to about shore 65D have been found to be particularly suitable for vertebral applications. If desired, these materials may be coated or impregnated with substances to increase their hardness or lubricity, or both.

In some embodiments, intermediate portion 16 has a generally cylindrical or tubular shaped body with a channel 30 extending longitudinally therethrough. Channel 30 may be appropriately sized and dimensioned for accommodating the coupling member or cord 18 therethrough. In the embodiment of FIG. 1, spacer 16 has a cylindrical profile and the external diameter 32 may be about the same as the diameter of flange 26 of end portions 12, 14. Alternatively, spacer 16 may be smaller or larger in diameter, or may be variable in diameter. According to one embodiment, intermediate portion 16 may range in length depending on the application or surgeon preference. For instance, spacer 16 may be between about 4 mm and 38 mm, and in a kit a multitude of differing lengths and dimensions may be provided. One skilled in the art will appreciate that the flexibility of the connection element 10 may be changed by the selection of the intermediate portion material and/or varying its dimensions.

Coupling member or cord 18 may be made from polyethylene terephthalateor (PET), ultra high molecular weight (WHMW) polyethylene such as Dyneema® or any other known material. The cord may also be formed using a braided or stranded wire or synthetic or any combination as desired. The strands may be formed from identical materials or may differ from each other. For example, one strand may he wire, whereas other strands may be rubber-based. In the embodiment of FIG. 1, cord 18 may also be made from, or additionally contain, an elastic material selected to allow the cord to elastically deform along its longitudinal axis. In this regard, depending on the selected material, cord 18 may elastically stretch or elongate along axis 20. In other embodiments, cord 18 may be designed to have a constant length so as to not stretch or elongate along its length. It will be clear to one skilled in the art that the structure, length and diameter of the coupling member will affect the flexibility of the connection element 10.

Figure 4:
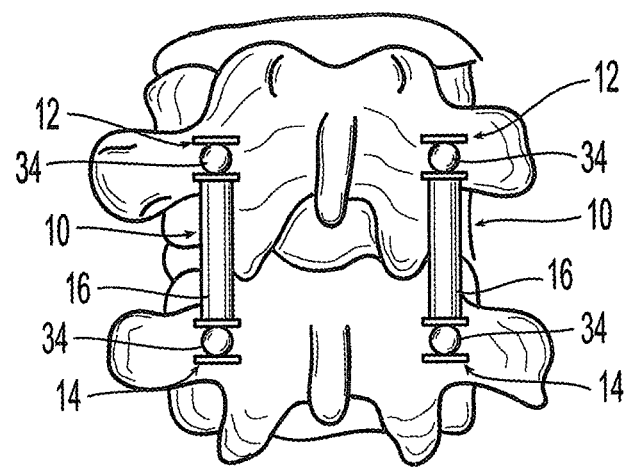
FIG. 4 is a posterior view of one embodiment of a spine stabilization system of the invention.

Referring to FIG. 4, when end portions 12, 14 are retained by respective bone fasteners 34, for example, and affixed to adjacent vertebrae, the connection element 10 provides stability while simultaneously permitting motion to the vertebrae in six degrees of freedom (i.e., x-axis, y-axis, z-axis, pitch, roll and yaw). Although the spacer 16 substantially limits the motion of the spools 12, 14 in the longitudinal axial direction, the compressibility of the spacer 16 and elasticity of cord 18 between the spools 12, 14 allows for stabilized motion of the spools 12, 14 in each of the six degrees of freedom while also providing a resistance and stability of motion in each of the six degrees of freedom. The intermediate portion 16 maintains the end portions 12, 14 in a substantially spaced relation, while allowing some relative movement of the spacer 16 when external forces cause the spacer body to bend or compress in any direction.

In some embodiments, the flexible connection element may be configured and adapted to exhibit preload forces even when the flexible portion is not undergoing externally applied torsional, axial, or bending loads. In this regard, the coupling member or cord 18 may be pre-tensioned so that the end portions 12, 14 are compressed against the intermediate portion 16 when engaged thereto. The amount of pre-tension can range from 0 to the tensile break strength of the coupling member of cord. The greater pre-tension loading of the cord generally results in a stiffer construct. This preloaded configuration may be beneficial for designing a preferential response to different types of external forces or loading. For instance, a preloaded flexible connection element may provide a greater resistance to torsional loads that would tend to further tighten the flexible connection element due to added frictional forces resisting sliding movement of the edges against each other.

Figure 5:
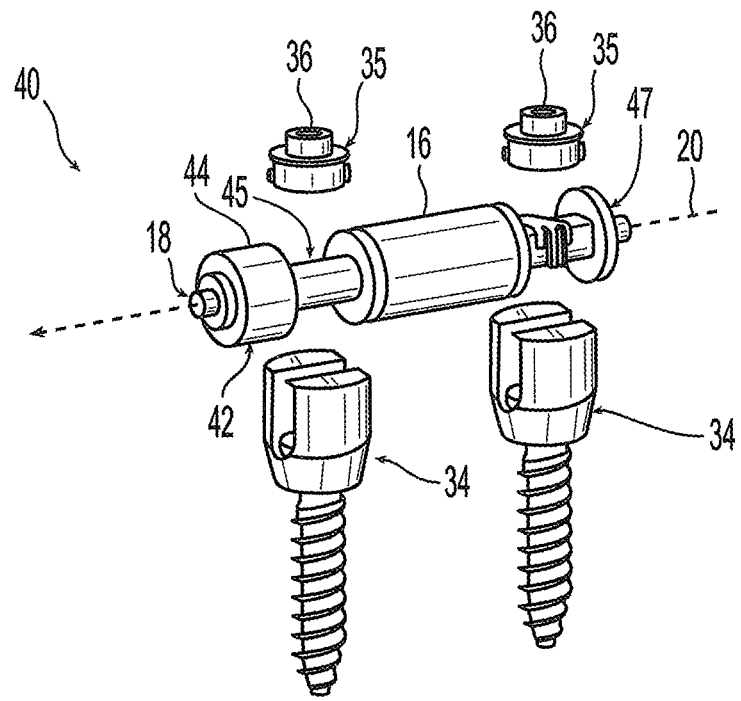
FIG. 5 is an exploded view of one embodiment of a stabilization system according to the invention with an alternate embodiment of a flexible connection element.
Figure 5A:
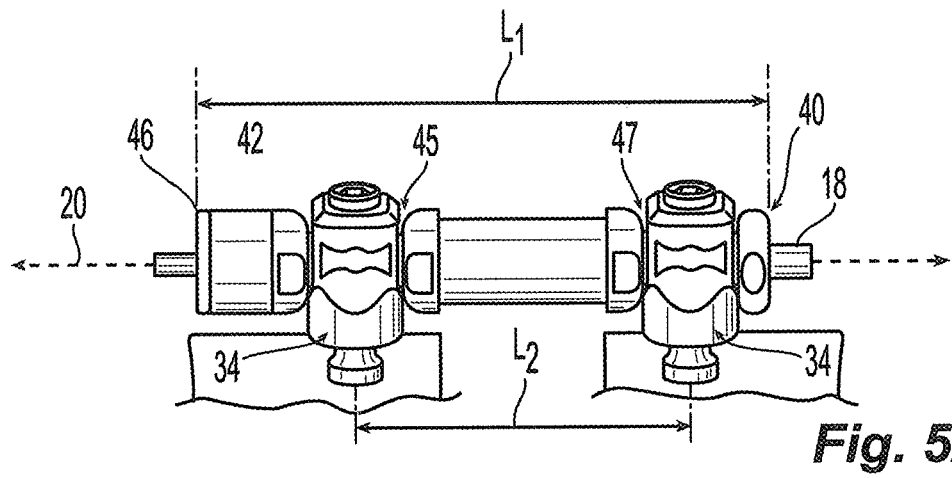
FIGS. 5A-5C are side views of the embodiment of FIG. 5 in a neutral position and extension positions.
Figure 5B:
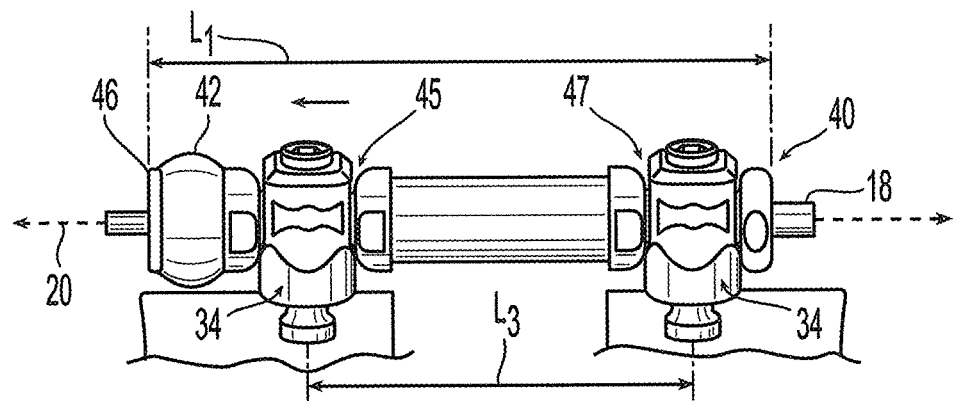
Figure 5C:
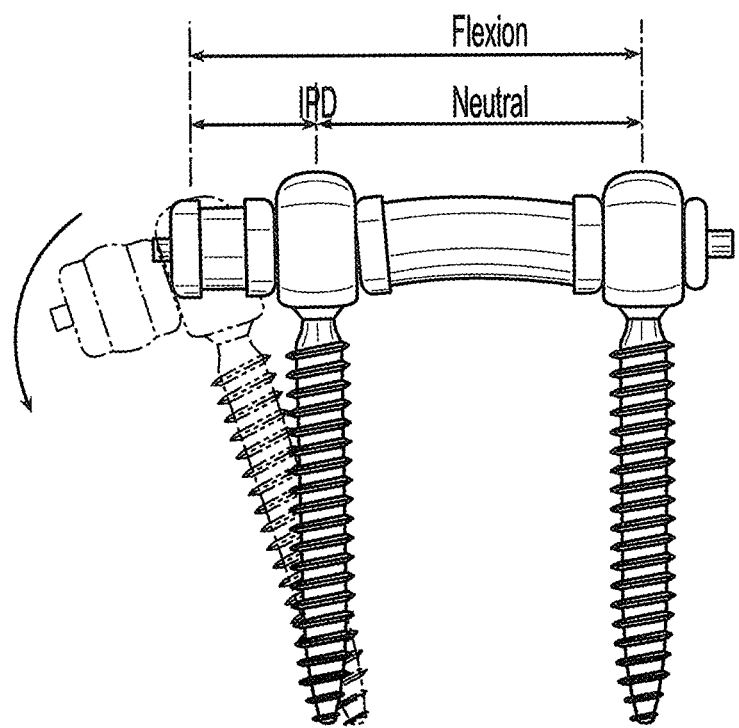

Referring to FIG. 5, in another embodiment of a flexible connection element 40, a bumper or other resiliently compressible member 42 may be disposed over cord 18 and positioned adjacent an outer end plate 44 of an end portion or spool 45. A rigid stop, flange, or end member 46 may be fixedly attached or clamped to cord 18 on the opposite side of bumper 42 from the spool 45. In this embodiment, spool 45 may be slidable, movable, or otherwise unconstrained with respect to cord 18. In this regard, bumper 42 may be resiliently compressed between spool 45 and stop 46 when spools 45, 47 are separated or forced apart in the longitudinal direction of axis 20. For example, referring to FIGS. 5A-5B, in one embodiment when spools 45, 47 are retained by respective bone fasteners 34 and affixed to adjacent vertebrae, such a configuration facilitates the separating movement between spools 45, 47 and the respective bone fasteners to which they are attached. Referring to FIG. 5A, showing connection element 40 in a first or neutral position with an overall length L1, spools 45, 47 may have a first separation distance L2. As shown in FIG. 5B, in a second position, after a separating movement between spools 45, 47, the second separation distance L3 is greater than L2 which replicates a change in the separation distance of the bone fasteners and the bone segments to which they are attached. Referring to FIG. 5C, one may appreciate that such a feature may be desired to replicate the natural kinematics that a spinal motion segment undergoes under flexion wherein the elongation of the intrapedicular distance typically occurs. In one variation, the flexible element may accommodate up to 8 mm of a change in intrapedicular distance under flexion. In another variation, up to 4 mm of a change in intrapedicular distance may be accommodated. Such elongation may be accomplished independent from or, in addition to, any elongation in cord 18. In this regard, the degree or extent to which flexible connection element 40 may elongate may be designed, preselected, or predicted with a greater degree of accuracy than reliance on elasticity or elongation in the cord alone. In one embodiment, bumper 42 may be made from the same material as intermediate portion 16. In alternate embodiments, bumper 42 may be made from a different material than intermediate portion 16 or bumper may be made from the same material and have a different hardness or flexibility than intermediate portion 16.

Figure 7:
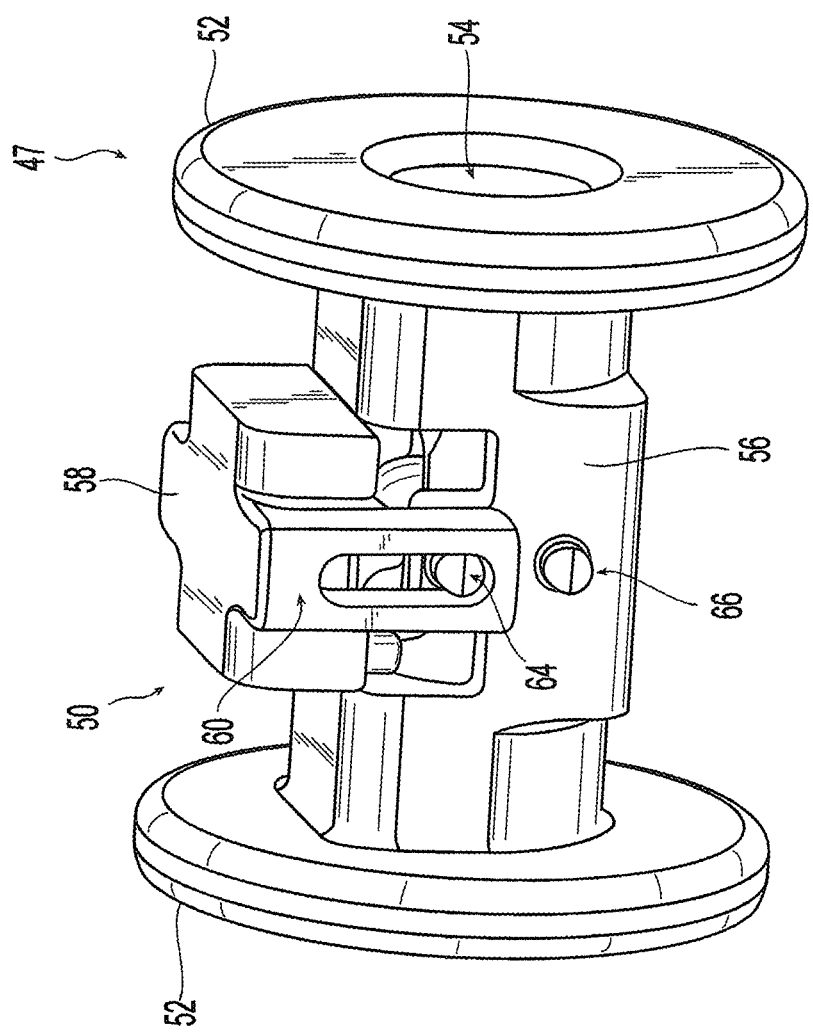
FIG. 7 is an assembled view of the end portion of FIG. 6 shown in a first position.
Figure 8:
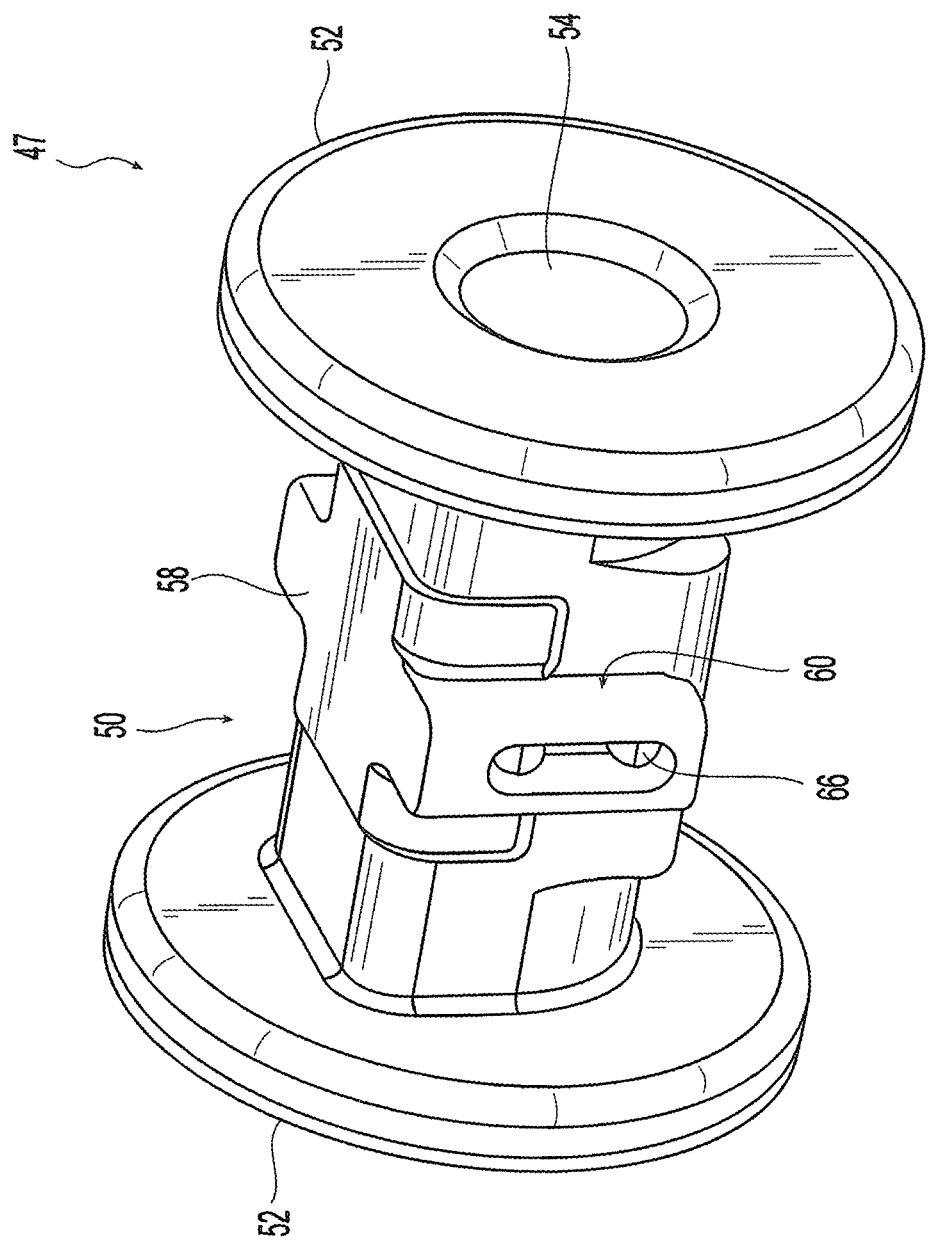
FIG. 8 is an assembled view of the end portion of FIG. 6 shown in a second position.

As shown in the embodiment of FIG. 5, an alternative end portion or spool 47 may be provided adjacent one end of flexible connection element 40. As best seen in FIGS. 6-7, spool 47 generally comprises a middle portion 50 interposed between outer end plates or flange portions 52. A central channel 54 extends axially through spool 47 and is generally configured and dimensioned to accommodate coupling member or cord 18. Middle portion 50 generally comprises a lower clamp body 56 and an upper clamp body 58 selectably moveable with respect to lower clamp body 56 to clamp down and affix cord 18 with respect to spool 47. In one variation, upper clamp body 58 has a pair of downwardly extending arms 60 having elongated openings 62 configured and dimensioned to receive protrusions or prongs 64, 66 extending outward from lower clamp body 56 so as to allow unidirectional one step clamping or locking of spool 47 with respect to cord 18. Arms 60 are configured and dimensioned to deflect or bend outward slightly to move over protrusions 64, 66. In this regard, protrusions 64, 66 may have a chamfer or angled outer surface 68 and arms 60 may have a chamfered, beveled, or angled inner lower surface 70 to facilitate arm deflection. Upper clamp body 58 may be first preassembled onto lower clamp body and positioned in a first position as shown in FIG. 7. In operation, as upper clamp body 58 is forced downward, the arms 60 may engage upper prongs 64 and deflect outward and over the upper prongs 64 such that the upper prongs extend through openings 60 and provisionally maintain upper clamp body 58 in the first position. As shown in FIG. 7, in the first position, upper clamp body 58 may be relatively loosely affixed to lower clamp body 56 such that a cord extending through middle portion 50 may slide or move with respect to spool 47. To affix or clamp cord 18 with respect to spool 47 upper clamp body 58 may be forced downward further onto lower clamp body 56 and positioned in a second or locked position as shown in FIG. 8. In operation, as upper clamp body 58 is forced downward, the arms 60 may engage lower prongs 66 and deflect outward and over the lower prongs 66 such that the lower prongs extend through openings 60 and maintain the upper damp body 58 in the second, clamped, or locked position. As shown in FIG. 8, in the second position, upper clamp body 58 may be relatively rigidly affixed to lower clamp body 56 such that a cord extending through middle portion 50 may not slide or move with respect to spool 47. One skilled in the art may appreciate that such a one step lock or clamping feature may be desirable to allow for tensioning of cord 18 during installation in situ. Referring again to FIG. 5, one my also appreciate that with such a clamping feature integrated into the middle portion 50 of spool 47, the step of clamping or locking the cord may be accomplished by finally tightening down on a cap 35 or set screw 36 of a pedicle screw assembly 34. In this regard, the tensioning and final clamping of cord 18 may be accomplished with a familiar procedure common to the installation of contemporary spinal stabilization systems.

Figure 8A:
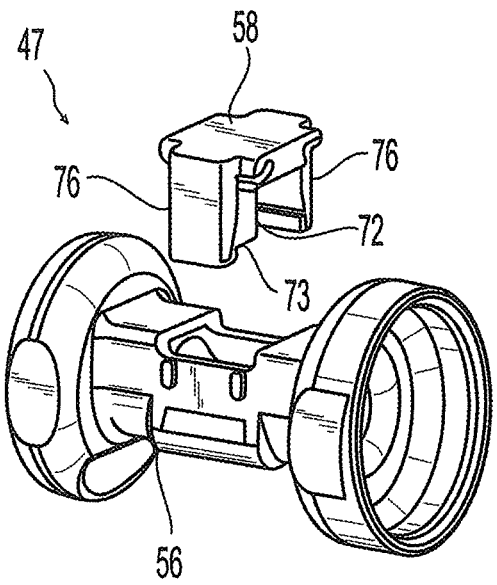
FIGS. 8A-8B are exploded perspective and exploded cross-sectional views, respectively, of an embodiment of another end portion of the flexible connection element of FIG. 5.
Figure 8B:
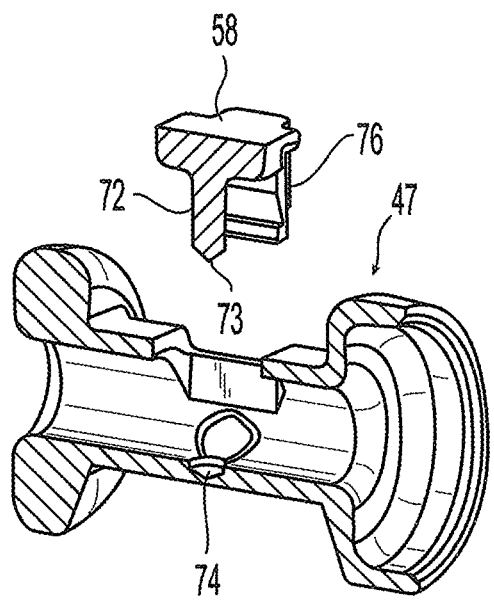
Figure 8C:
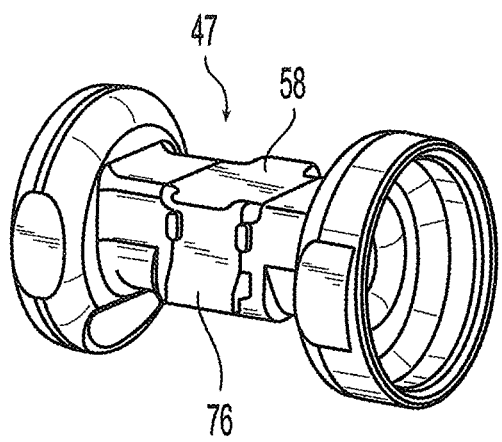
FIGS. 8C-8D are assembled perspective and assembled cross-sectional views, respectively, of the embodiment of FIGS. 8A-8B.
Figure 8D:
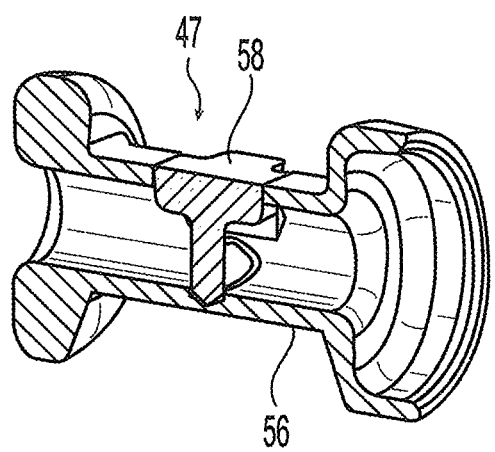

Referring to FIGS. 8A-8D, another embodiment of a spool. 47 is disclosed which generally comprises a post or piercing means to affix cord 18 with respect to spool 47. In one variation, upper clamp body 58 has a central finger or post 72 extending downwardly from the underside thereof. In one variation, the post 72 may be configured and dimensioned to extend through the cord 18 so as to puncture or pierce through cord 18 and the distal tip 73 of post 72 may enter into a depression 74 provided on the interior of lower clamp body 56. As with the above described embodiment, a pair of arms 76 extend downward from upper clamp 58 are configured and dimensioned to engage lower clamp body 56 so as to allow unidirectional one step clamping, piercing, and/or locking of spool 47 with respect to cord 18. As shown in FIGS. 8A-8B, in a first position, upper clamp body 58 may be spaced from or relatively loosely affixed to lower clamp body 56 such that a cord extending through middle portion 50 may slide or move with respect to spool 47. To affix or clamp cord 18 with respect to spool 47 upper clamp body 58 may be forced downward further onto lower clamp body 56 and positioned in a second or locked position as shown in FIGS. 8C-8D. As shown in FIGS. 8C-8D, in the second position, upper clamp body 58 may be relatively rigidly affixed to lower clamp body 56 such that a cord extending through middle portion 50 may not slide or move with respect to spool 47.

Referring to FIGS. 9-12, one embodiment of a clamp assembly 80 for clamping rigid stop, flange, or end portion 46 to cord 18 is shown. Clamp assembly 80 generally comprises an annular end body 82 having an end plate or flange 84 and a central cavity 86 configured and dimensioned to house a lower clamp body 88 and an upper clamp body 90. Upper and lower clamp bodies 90, 88 have a tapered or partially conically shaped outer surface 92 configured to engage, slide, mate, wedge, or otherwise contact a corresponding opposing tapered or shaped. interior wall surface 94 of cavity 86. Upper clamp body 90 is movable with respect to lower clamp body 88 to clamp down and affix cord 18 with respect to end body 82. In one variation, upper clamp body 90 has a pair of downwardly extending arms 96 having openings 98 configured and dimensioned to receive protrusions or prongs 100 extending outward from lower clamp body 88 so as to allow unidirectional clamping or locking of end 46 with respect to cord 18. Arms 96 are configured and dimensioned to deflect or bend outward slightly to move over protrusions 100. To affix or clamp cord 18 with respect to end 46, upper clamp body 90 may be assembled over lower clamp body 88 with cord 18 positioned therebetween. As shown in FIG. 12, cord 18 may be additionally cinched, clamped, or locked when the assembled upper and lower clamp bodies 90, 88 are positioned within cavity 86 and pulled or forced longitudinally against the tapered inner wall 94 such that the outer surface 92 engages, slides, mates, or wedges thereagainst to force the upper and lower clamp bodies 90, 88 to contract upon cord 18 such that a cord extending through the clamp bodies 88, 90 may not slide or move with respect to end 46. One skilled in the art may appreciate that such a tapered arrangement facilitates secure clamping during natural movement of flexible connection element 40 when installed. In one variation, a shoulder portion 102 of end body 82 may extend outward from flange 84 and may extend into a portion of bumper 42.

Referring to FIGS. 12A-12D, another embodiment of a clamp assembly 104 for clamping rigid stop, flange, or end portion 46 to cord 18 is shown. Clamp assembly 104 generally comprises an annular end body 82 having a central cavity 86 and an end plate or flange 84 configured and dimensioned to house an insertable clamp body 105. Clamp assembly 104 generally comprises a post or piercing means to affix cord 18 with respect to end portion 46. In one variation, insertable clamp body 105 has a central finger or post 106 extending downwardly from the underside thereof. In one variation, the post 106 may be configured and dimensioned to extend through the cord 18 so as to puncture or pierce through cord 18 and the distal tip 107 of post 106 may enter into a depression 108 provided on the interior of central cavity 86. Insertable clamp body 105 is movable with respect to clamp body 82 to puncture, pierce and/or clamp down and affix cord 18 with respect to end body 82. In one variation, insertable clamp body 105 has a pair of arms 109 configured and dimensioned to engage clamp body 82 so as to allow unidirectional one step clamping, piercing, and/or locking of end portion 46 with respect to cord 18. As shown in FIGS. 12A-12B, in a first position, insertable clamp body 105 may be spaced from or relatively loosely affixed to end body 82 such that a cord extending through cavity 86 may slide or move with respect to end body 82. To affix or clamp cord 18 with respect to end portion 46, insertable clamp body 105 may be forced downward further onto end body 82 and positioned in a second or locked position as shown in FIGS. 12C-12D. As shown in FIGS. 12C-12D, in the second position, insertable clamp body 105 may be relatively rigidly affixed to end body 82 such that a cord extending through cavity 86 may not slide or move with respect to end portion 46.

Figure 13:
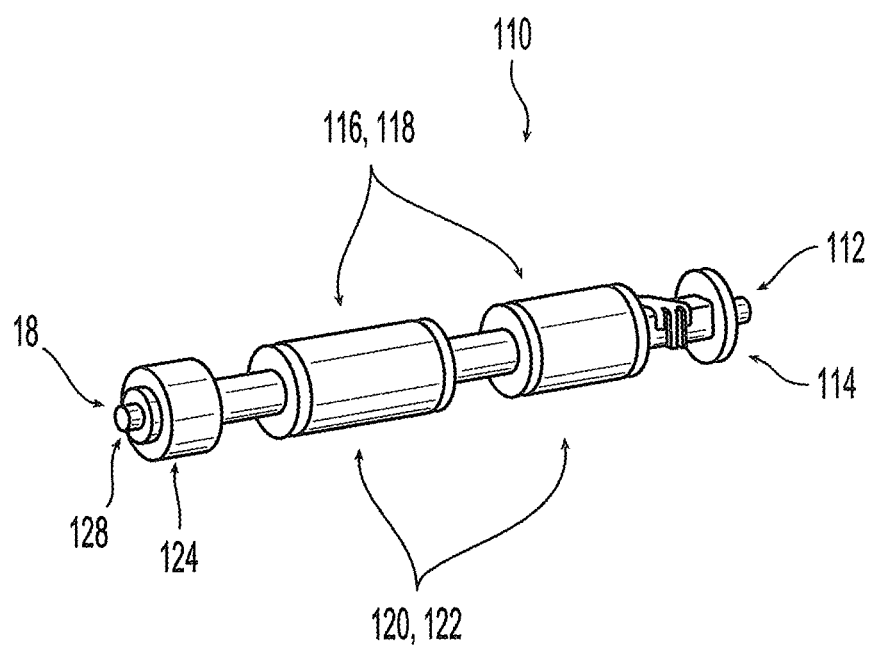
FIG. 13 is a perspective view of another embodiment of a flexible connection element.

In general the flexible connection elements described herein can be extended to stabilize two or more joints or spinal motion segments between three or more adjacent vertebrae, and affixed to respective vertebrae by three or more fasteners. Thus, in one exemplary embodiment, shown in FIG. 13 a flexible connection element 110, similar to connection element 40 of FIG. 5 includes a plurality of spacers for providing flexible stabilization to a plurality of joints or spinal motion segments. In the embodiment of FIG. 13, a constrained spool 112 may be provided at a first end 114, and unconstrained spools 116, 118 and spacers 120, 122 may be interposed between a bumper 124 and clamp assembly 126 disposed on a second end 128. Additionally, the spacers 120, 122 may be alternated with various spool members (i.e. constrained or unconstrained) in any order or combination as needed by the surgeon. Further, an additional bumper may be positioned outside the first end such that a bumper would be provided at opposite ends of the construct. In this way, a hybrid multi-level or multi-spine segment connection unit may be designed, wherein each segment of the connection unit can provide a desired level of flexibility suited for each respective pair of inferior and superior vertebrae to be stabilized. For example, a first section of the connection unit that stabilizes a first pair of vertebrae may be very rigid, while a second section of the connection unit that stabilizes a second pair of vertebrae may be more flexible when compared to the first section. Numerous desired combinations of sections may be achieved to create a hybrid multi-level or multi-segment connection unit, in accordance with the present invention.

Figure 14:
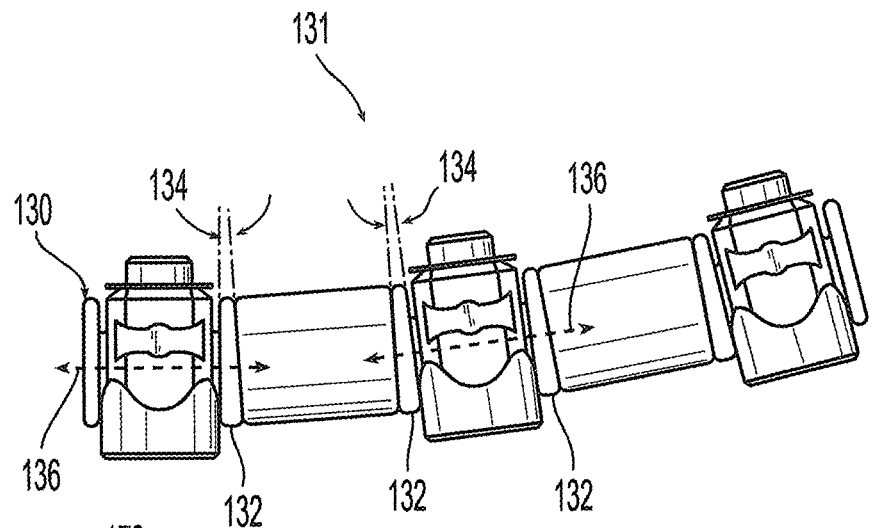
FIG. 14 is a side view of another embodiment of a flexible connection element.

Referring to FIG. 14, in one aspect of the invention one or more angled or lordosed spools 130 may be provided to form a construct or flexible connection element 131 to conform to and/or restore the natural lordosis of the spine. Spools 130 may be similar to spools 45, 47 described above except the end plates or flanges 132 may have an angle 134 or be tapered with respect to the normal of longitudinal spool axis 136. In one embodiment, the angle 134 of the end plate 132 is between about 3.5 degrees and about 5 degrees. In one variation, the end plate 132 may be angled about 4 degrees.

Figure 15:
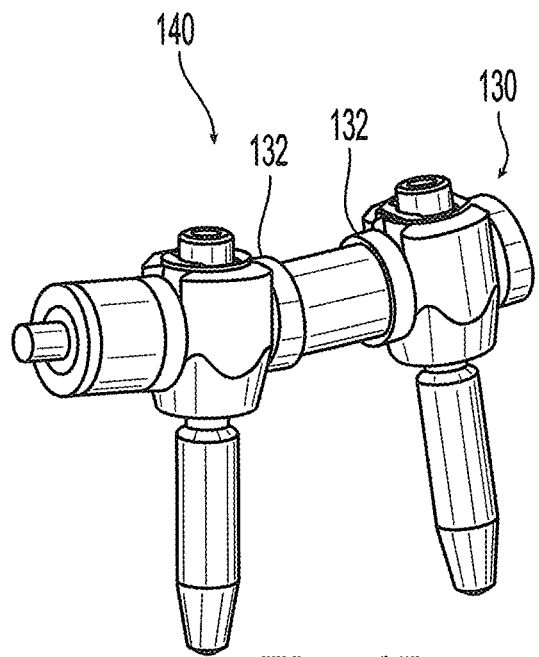
FIGS. 15-16 are perspective views of alternate embodiments of stabilization systems according to the invention each with alternate embodiments of a flexible connection elements.
Figure 16:
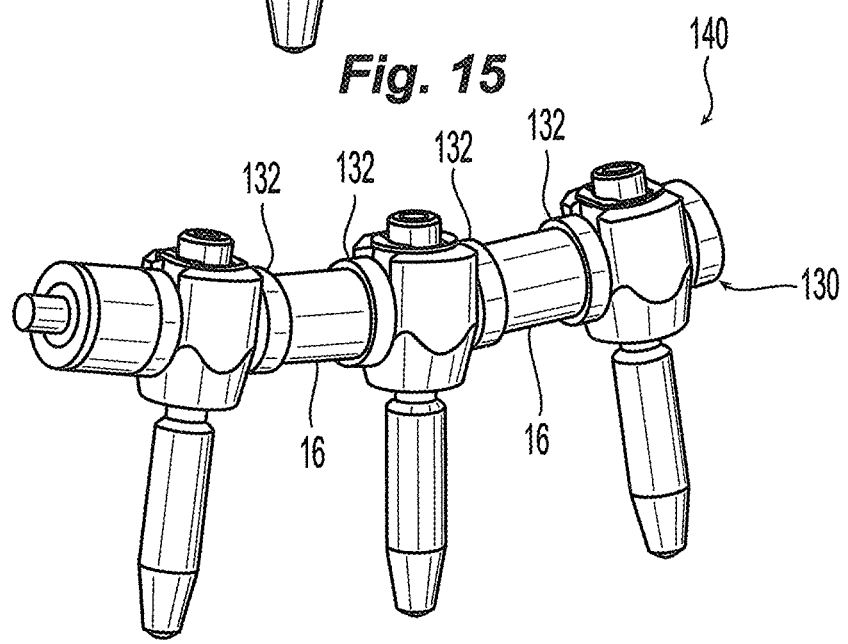

Referring to FIGS. 15-16, single and multi-level versions of another embodiment of a flexible connection element 140 are shown. Flexible connection element 140 is similar to connection element 131 of FIG. 14 except the end plates or flanges 132 of spools 130 are configured and dimensioned to extend over at least a portion of the adjacent intermediate portion or spacer 16. In this regard, end plates 132 of spools 130 may have a cylindrical internal portion 142 configured and dimensioned to house an end of the adjacent spacer 16. One skilled in the art may appreciate that such a configuration may resist shear translational forces when implanted adjacent a motion segment of the spine. Such an end plate feature may be provided on spools or end portions with or without lordosis or in any other embodiments of end portions described herein.

Figure 17:
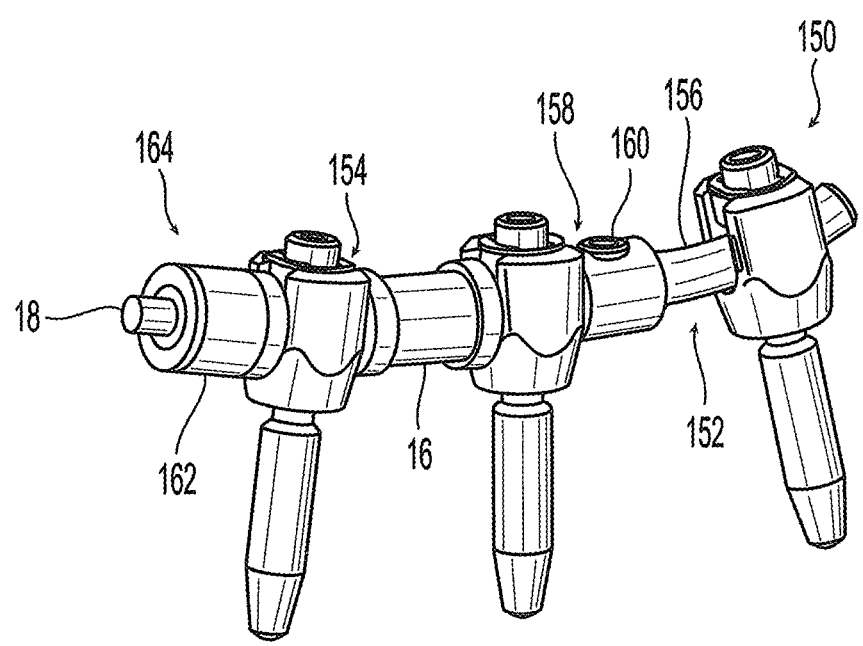
FIG. 17 is a perspective view of another embodiment of a stabilization system.

Referring to FIG. 17, another embodiment of flexible connection element 150 is shown. Connection element 150 may be employed in a hybrid procedure employing fusion and dynamic stabilization. In this regard, an elongated end portion 152 may be provided and engaged between vertebrae to be fused and one or more adjacent vertebral levels can be dynamically stabilized with the intermediate portion 16 engaged between end portions 152, 154. End portion 152 may have a rod portion 156 integrated into a spool portion 158 and may include a clamping means 160, such as a set screw, to affix cord 18 to end portion 152. In addition, a bumper 162 may be provided adjacent a second end 164 to facilitate elongation of the dynamically stabilized Connection elements are also contemplated that would provide for multiple spine levels stabilized by fusion and multiple levels dynamically stabilized.

Figure 18:
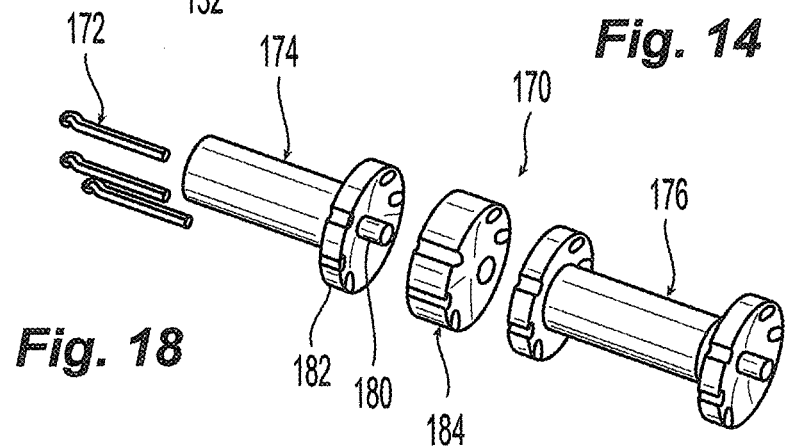
FIG. 18 is an exploded view of another embodiment of a flexible connection element.

Referring to FIG. 18, another embodiment of a flexible connection element 170 is shown. Flexible connection element 170 may have one or more cords 172 extending longitudinally between rigid end portions 174, 176 and the one or more cords 172 may be tied or crimped into holes 178 provided on end portions 174, 176. A central protrusion, prong, or nub 180 may extend outward from the face of end plate or flange 182 and into flexible intermediate portion 184 to enhance the physical interconnection of the intermediate portion 184 to end members 174, 176.

Figure 19:
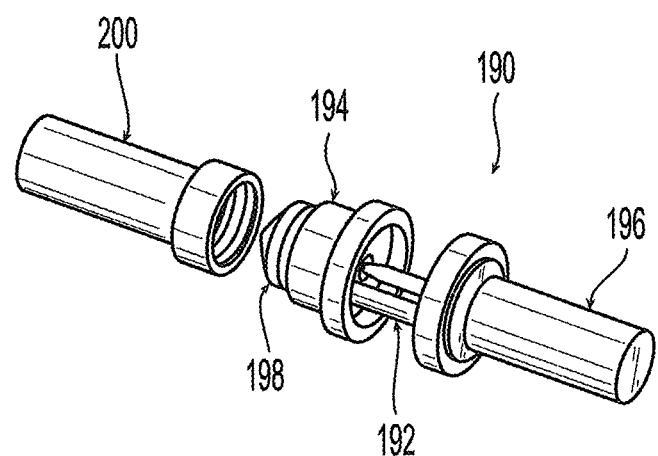
FIG. 19 is an exploded view of another embodiment of a flexible connection element.

Referring to FIG. 19, an alternate embodiment of a flexible connection element 190 is shown wherein one or more cords 192 extend through intermediate portion 194 and may be rigidly attached to a first end portion 196 and a threaded member 198. Threaded member 198 may be screwed or threadedly attached to a second end portion 200. In this regard, threaded member 198 may be rotatably advanced to change the amount of tension in the cords and thus alter the stiffness of the construct of flexible connection element 190.

Figure 20:
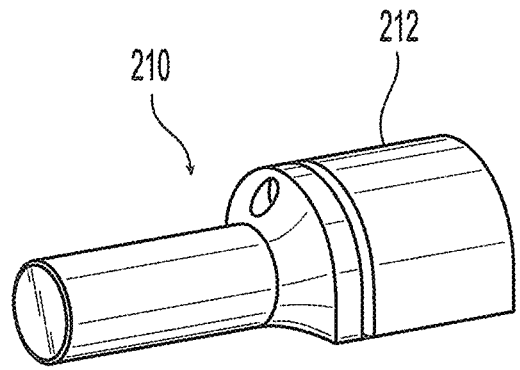
FIGS. 20-22 depict an alternate end portion of a flexible connection element according to the invention.
Figure 21:
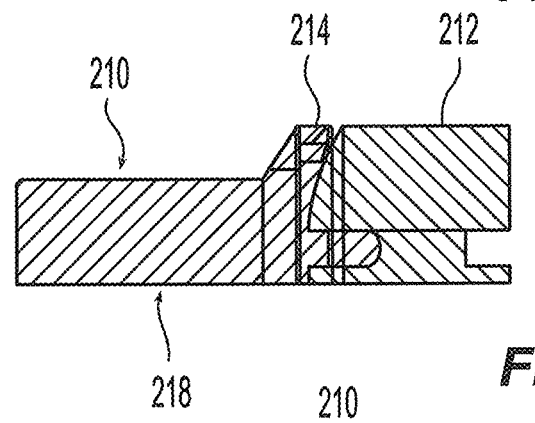
Figure 22:
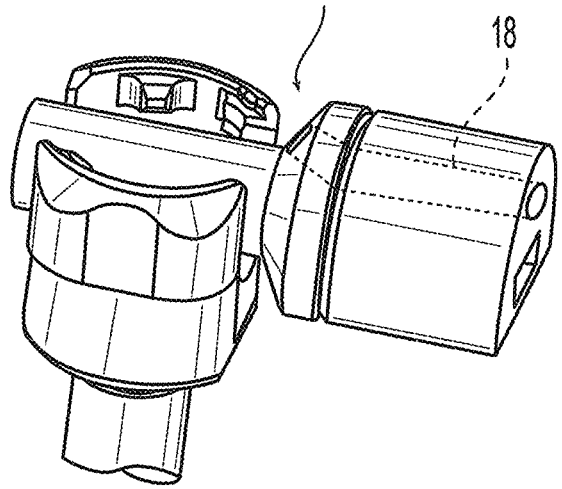

Referring to FIGS. 20-22, another embodiment of an end member or portion 210 and intermediate portion 212 of a flexible connection element is shown. In this embodiment, end member 210 has a generally spherical seat or interface surface 214 that is configured to engage or contact intermediate portion 212. In another aspect of the invention, a protrusion 216 may extend from interface surface 214 and extend into intermediate portion 212 to enhance the physical interconnection of the intermediate portion 212 to end member 210. In a further aspect, the anterior portion or bottom 218 of end member 210 and intermediate portion 212 may be flat to facilitate a low profile once installed. It is also contemplated that such a flat bottom feature may be incorporated in the many alternate embodiments described throughout the specification. In a further aspect, a coupling member or cord 18 may extend eccentrically through intermediate portion 212. For example, in the depicted embodiment, cord 18 may extend through intermediate portion adjacent the upper or posterior portion of spacer. In this regard, the flexible connection element constructed in such a fashion may be less rigid on one side as compared to the other.

Figure 23:
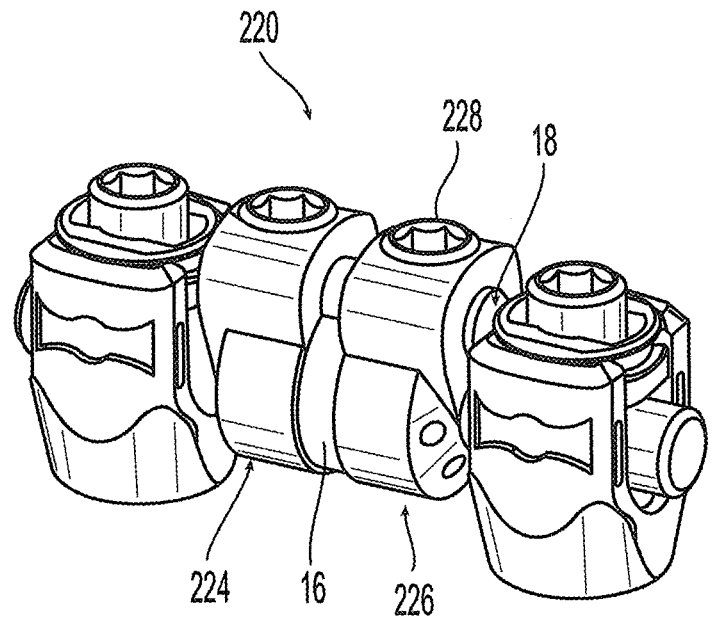
FIG. 23 is a perspective view of another flexible connection element.

Referring to FIG. 23, an alternate embodiment of a flexible connection element 220 is shown wherein the coupling member or cord 18 extends along the top or posterior side of intermediate portion 16 and may be secured or affixed to end members 224, 226 by a top mounted set screw lock 228. As a result, like previously described embodiments the flexible connection element constructed in such a fashion may be less rigid on one side as compared to the other.

Various embodiments of flexible connection elements contemplate alternative end members or portions configured to engage alternative bone fasteners or anchors. In particular, the embodiments of FIGS. 24-54, discussed below, are generally configured to engage a post type anchor or bone screw. In general, these embodiments have at least one end portion comprising a hole or opening configured to receive the posted end of the bone anchor therethrough. However, one skilled in the art may appreciate that these embodiments may be modified to engage a top loading, yoke, or tulip type receiving member of an anchor.

Figure 24:
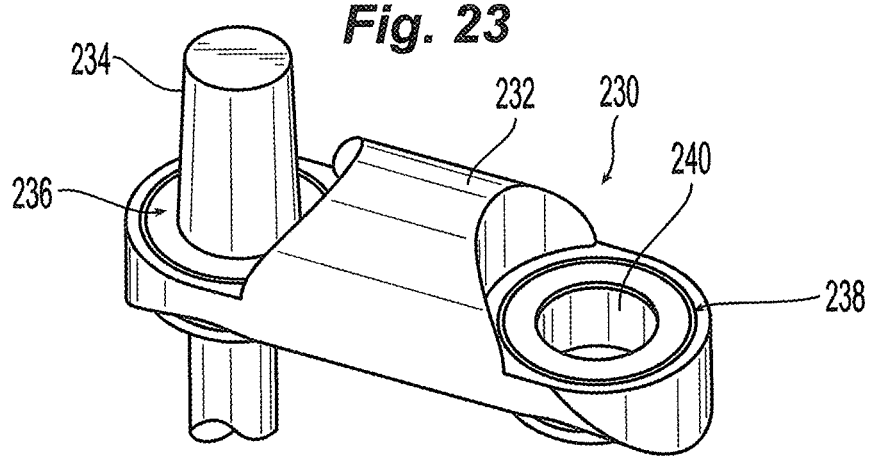
FIGS. 24-25 are perspective and cross-sectional views, respectively, of another embodiment of a flexible connection element.
Figure 25:
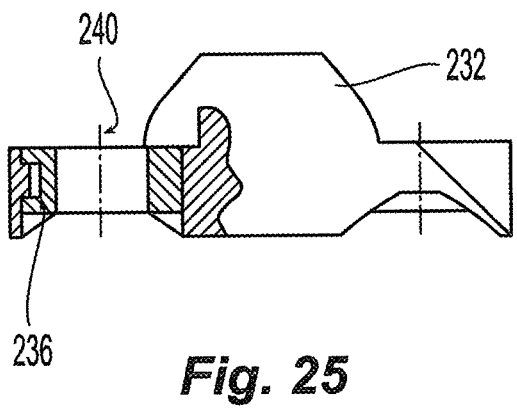

Referring to FIGS. 24-25, another embodiment of a flexible connection element 230 is shown that is configured and dimensioned to engage a posted screw or bone fastener. According to one variation, the flexible connection element 230 may comprise an intermediate body portion 232 interposed between opposite end portions 236, 238. Intermediate body portion 232 may be made from a similar resiliently deformable material as intermediate portions described above and may be molded over and between end portions 236, 238. In one aspect of the embodiment, end portions 236, 238 may define a generally cylindrical opening 240 to accommodate a shaft therethrough, such as a shaft or post end of a posted screw fastener. In this regard, flexible connection element 230 is generally configured and dimensioned to be coupled to and to interconnect between two bone fasteners, one coupled to each end portion 236, 238. In one variation, end portions 236, 238 may each comprises rigid sleeves or annular rings which may be encapsulated or molded into the material of the intermediate body portion. For example, if intermediate body portion is made from a polymer material, the polymer may be molded over annular rings 236, 238. In another aspect, intermediate body portion 232 may have a rounded profile and may extend in the posterior direction a sufficient distance to cover or extend beyond a nut or other clamping member assembled upon the posted screw and engaging end portions 236, 238. In general, When a nut or clamping member is assembled upon the end or post portion of anchor 234, it sits down in a low profile position. In one variation, flexible connection element 230 may elongate and compress due to the elastic or resilient properties of the material of the intermediate portion without an integrated coupling member or cord. In alternate embodiments, one or more coupling members or cords may be provided extending about end portions 236, 238 and may or may not he molded into intermediate portion 232 to facilitate the flexible movement of connection element 230.

Figure 26:
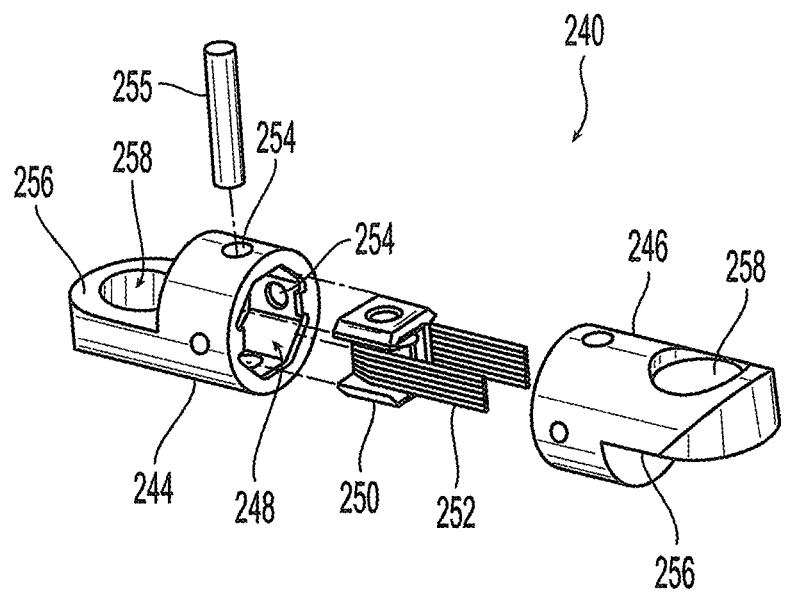
FIG. 26 is an exploded view of another embodiment of a flexible connection element.

Referring to FIG. 26, another embodiment of a flexible connection element 240 is shown wherein the intermediate portion or spacer (not shown) may be molded between end portions 244, 246. In this embodiment, end portions 244, 246 generally have an opening 248 to house a mounting block 250 and one or more cords 252 may be fixed to the end portion 244 by mounting block 250. Mounting block 250 may be pinned into the housing 248 by a post or pin member 255. In one variation, one or more side holes 254 may be provided in the housing 248 to allow the spacer material to flow out through the openings during injection molding to mechanically lock the housing 248 to the intermediate portion. In one embodiment, the cord or cords 252 may be locked into block 250 by winding. The cord or cords 252 may be aligned in a medial/lateral or anterior/posterior direction. In this embodiment, the flexible connection element 240 may elongate due to the flexible properties of the cord itself. In one variation, the end portions 244, 246 may have a flat section 256 surrounding an opening 258 in the end portion to accommodate multi-level stacking or serial connection in the spine. In this regard, the flexible connection elements 240 may be flipped over or juxtaposed to facilitate face to face contact of flat sections 256 and nesting of each flexible connection element 240. One skilled in the art may appreciate, that such a feature facilitates a low profile construction in addition to allowing for implantation over multiple levels.

Figure 27:
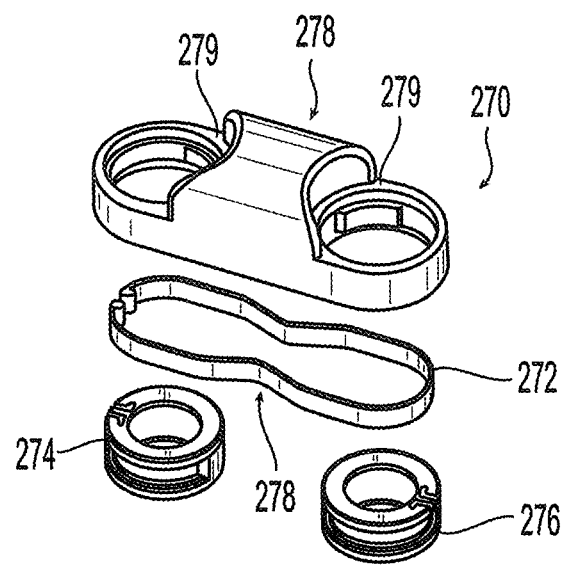
FIG. 27 is an exploded view of another embodiment of a flexible connection element.

FIG. 27 is a perspective view of another embodiment of a flexible connection element 270. In this embodiment, a generally flattened band 272 may extend around end spools 274, 276 and about the periphery of the connection element 270. A spacer body 278 may be made from a similar resiliently deformable material as intermediate portions described above and may be molded over and between end spools 274, 276 and band 272. In one variation, band 272 may be made from a metal material such as titanium, spring steel, or other suitable material. According to one aspect, in this embodiment, band 272 may have one or more bends 278 or crimps along its length to allow for elastic deformation of the band 272 and/or separation or retraction of end portions 274, 276 and facilitating the return to the default position or configuration. In another variation, cover or spacer body 278 may facilitate elastic deformation under compressive forces (i.e. when spools 274, 276 are forced closer together). In this regard, the cover body 278 may resiliently deform to block the compressive movement and after the compressive force dissipates the cover body 278 may restore itself to its original shape, thereby restoring the spacing between spools 274. 276 and the screws attached thereto. Like the embodiment of FIG. 26, described above, flexible connection element 270 may comprise a single segment in a multilevel construct. In this regard, the end portions 274, 276 may be juxtaposed to facilitate face to face contact of generally flat sections 279.

Figure 28:
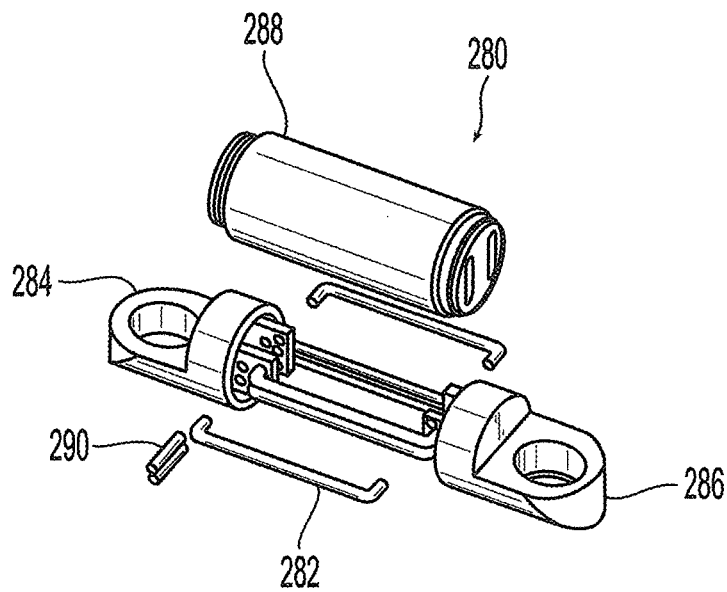
FIG. 28 is an exploded view of another embodiment of a flexible connection element.

Referring to FIG. 28, in a modification of the embodiment shown in FIG. 26, flexible connection element 280 may have one or more cords 282 extending longitudinally between end portions 284, 286 and the one or more cords may be tied or crimped into holes 288 provided on end members 284, 286. The flexible intermediate portion 288 may be molded around pins 290 to enhance the physical interconnection of the intermediate portion 288 to end members 284, 286. According to this embodiment, intermediate portion 288 may have a generally cylindrical shape with a generally circular cross-section.

Figure 29:
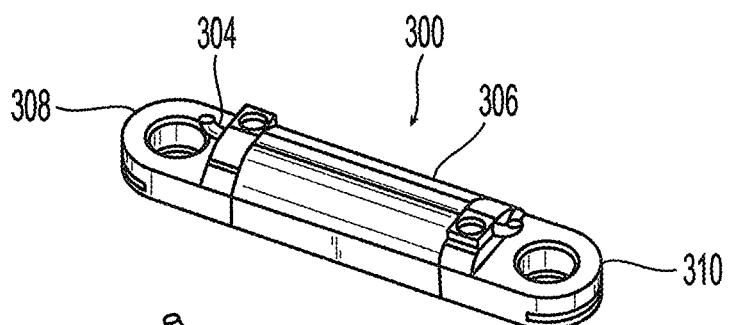
FIGS. 29-30 are perspective and exploded views, respectively, of another embodiment of a flexible connection element.
Figure 30:
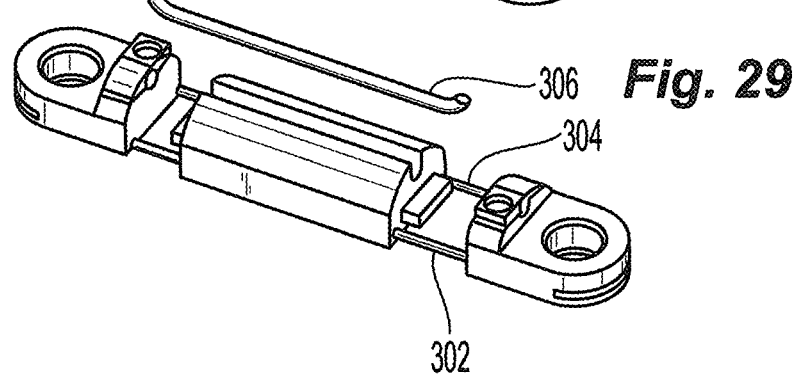

Referring to FIGS. 29-34, various alternative cord connection mechanisms are shown. In the embodiment of FIGS. 29-30, at least three cords 301, 302, 304 are provided with at least two cord portions 302, 304 extending along the lower, bottom or anterior portion and at least one cord portion 300 along the upper, top, or posterior portion of intermediate section 306. As with previous embodiments, intermediate section 306 may be made from an elastically resilient deformable material such as polycarbonate urethane or the like and the end members 308, 310 may be made from a suitable rigid material such as titanium or the like. Cord 301 provided along the upper portion of intermediate section 306 may be selectively lengthened or shortened prior to implantation to shape the flexible connection element 300 to accommodate lordosis. In this regard, if the upper cord portion 301 is shortened the flexible connection element 300 will bow or curve in the posterior direction. In another variation, the lower cord portions 302, 304 may be parts of a single loop of cord extending around the periphery of end members 308, 310 of the flexible connection element 300. In addition, one may appreciate that such a configuration may provide different levels of stiffness in the anterior-posterior direction. This may be advantageous if it is desired to provide a greater level of stiffness when the flexible connection element 300 is flexed during spinal extension (e.g., when a patient bends backward) and a lesser level of stiffness when the flexible connection element 300 is flexed during spinal flexion (e.g., when a patient bends forward). Thus, flexible connection element 300 can provide different levels of stiffness in different directions of movement and, hence, varying levels of stability can be provided to different directions of movement of a vertebra secured thereto.

Referring to FIGS. 31-32, in a modification of the embodiment shown in FIGS. 29-30, upper cord 301 may be coupled or fixed to end members 308, 310 with a mechanical spring biased binding mechanism or member 320 similar to a karabiner. Referring to FIGS. 33-34, in another modification of the embodiment shown in FIGS. 29-30, cords 302, 304 may be moldably attached to end members 308, 310 and an upper cord 301 may be fixedly attached with one or more set screws 324 and hence adjusted or tensioned to create lordosis as explained above. Bottom or lower cords 302, 304 may have enlarged lead ends 326 configured and dimensioned to fit or key into corresponding eye holes 328 in end members 308, 310.

Referring to FIG. 35, a saggital plane view shows a plurality of flexible connection elements 300 similar to the embodiment shown in FIGS. 33-34 situated in a serial juxtaposed position to form an exemplary multilevel construct. In this regard the adjacent flexible connection elements are flipped, or inverted to facilitate a face to face positioning or contact of flat sections 330 of end portions 308, 310. One skilled in the art may appreciate that a post or shaft portion 336 of a bone fastener or screw may extend through two adjacent flexible connection elements.

Referring to FIGS. 36-37, in a modification of the embodiment shown in FIGS. 33-34, end member 362 of flexible connection element 360 may have a flexible slit 364 that is compressible on a posted type screw or bone fastener. In this regard, the flexible slit 364 comprises a deflectable or deformable portion configured and dimensioned to deform, collapse, or compress to engage with a spherical or ball shaped feature that may be provided, for example, on a shaft of a post type screw. In operation, the end member 362 of this embodiment may be secured to a post type fastener without the need for more than one nut or clamping member when two end members are attached to a single post type screw. One skilled in the art may appreciate that such a configuration may facilitate the stacking or juxtaposition of flexible connection elements 360 in a multilevel construct as shown in FIG. 35.

Referring to FIG. 38, another embodiment of an end member 380 is shown. In this embodiment, a modified protrusion, rib, or key portion 382 extends from internal face 384 of end member 380. Similar to previous described embodiments, protrusion 382 is configured and dimensioned to mate, extend into, or otherwise engage a correspondingly shaped indentation in an intermediate portion and to mechanically interface or connect therewith. In this variation, protrusion 382 has a generally arcuate or curved convex surface 386 extending in the anterior-posterior direction and has generally flat or planar side walls 388. In operation, curved surface 386 generally facilitates rotational or pivotal relative movement in the anterior posterior direction between end member 380 and an intermediate portion. Side wails 388 meanwhile generally prohibit relative movement between the end member and the intermediate portion in a medial-lateral direction.

Referring to FIGS. 39-41 additional embodiments of flexible connection elements 390 are shown. As best seen in FIG. 40 wherein one variation of a bottom portion of a clamp member is shown, clamp member 392 defining one or more generally spherical socket portions 394 may be provided to clamp or hold a ball shaped end member 396 of flexible connection element 390. The ball shaped end member 396 allows selectably fixable angulation of flexible connection element 390 with respect to a post type screw as shown in FIG. 39. Once a desired angle is selected, the clamp member 392 may be compressed by, for example, a nut 398 to clamp down and affix end member 396 within socket portion 394. According to one embodiment, once the clamp member 392 is so affixed, no further movement or angulation between clamp member 392 and end member 396 is contemplated to occur without loosening or unclamping clamp member 392. Referring to FIG. 41, in a modification of the embodiment of FIG. 39, clamping member 392 of flexible connection element 400 may have socket portions offset from the longitudinal axis 402.

Figure 42:
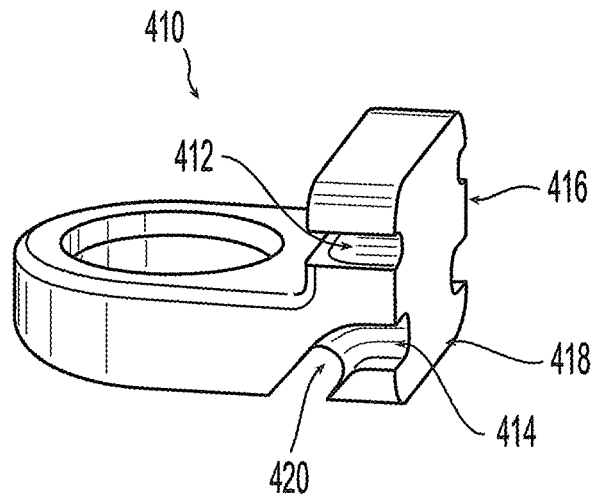
FIG. 42 is a perspective view of another embodiment of an end portion according to the invention.

FIG. 42 depicts another embodiment of an end member 410. In this embodiment, modified grooves, passageways, slots or indentations 412, 414 are provided to accommodate the extension of a coupling member or cord therethrough or thereabout. In this regard, a posterior groove 412 extends about the outer periphery of an upper portion 416 and is generally configured and dimensioned to accommodate, hold, or capture a posterior cord loop. An anterior groove 414 extends about the outer periphery of a lower portion 418 with a generally angled downward section 420 adjacent the lateral edges. Like posterior groove 412, anterior groove 414 is generally configured and dimensioned to accommodate, hold, or capture an anterior cord loop.

Figure 43:
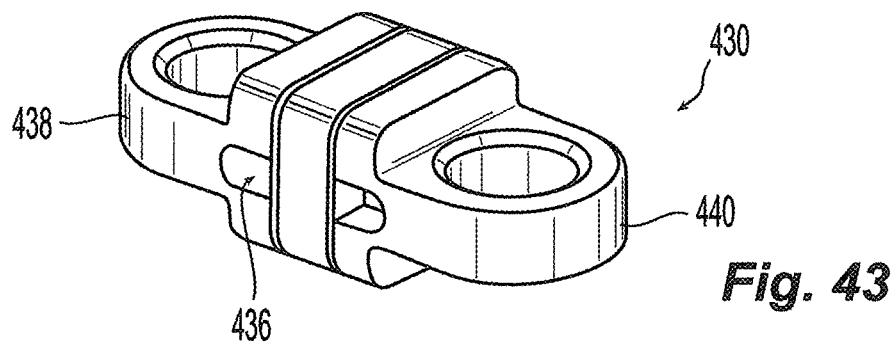
FIGS. 43-45 are perspective, top, and cross-sectional views, respectively, of another embodiment of a flexible connection element.
Figure 44:
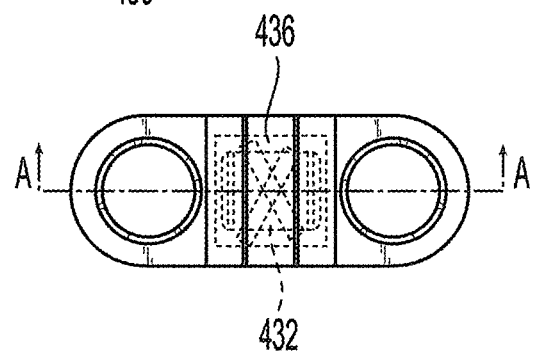
Figure 45:
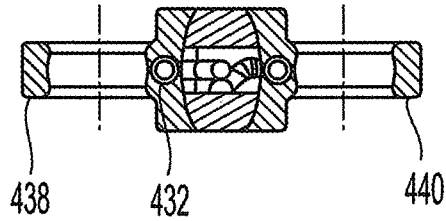

Referring to FIGS. 43-45, another embodiment of flexible connection element 430 is shown wherein the coupling member comprises a looped cord 432 having an internal twist or crossed over portion. Intermediate portion 434 has an internal opening 436 configured and dimensioned to provide clearance or space to allow cord 432 to twist and tension. One skilled in the art may appreciate that the more cord 432 twists, the shorter the distance between end members 438, 440 may get, and hence the overall tension or stiffness of the construct may correspondingly increase. In this regard, the overall tension or stiffness of the construct may be controlled.

Figure 46:
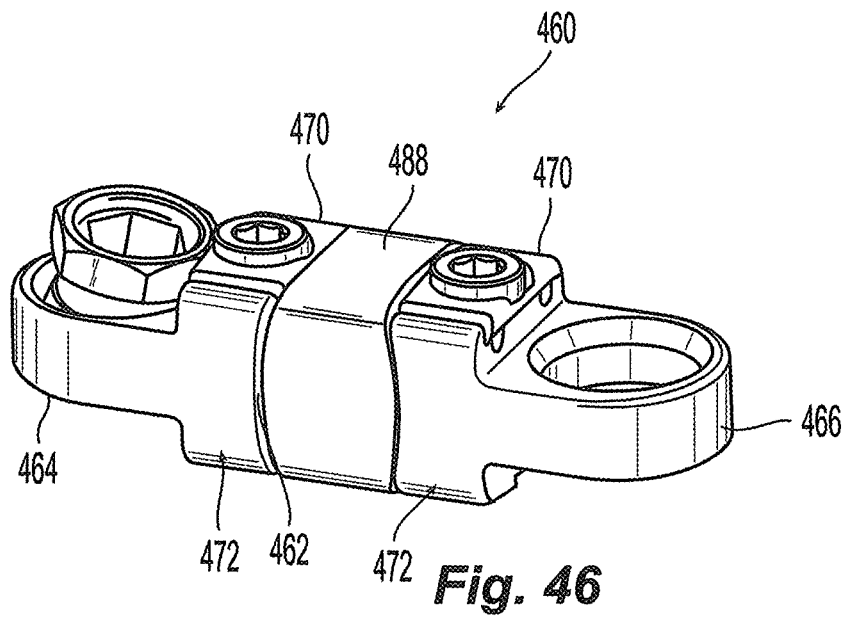
FIG. 46 is a perspective view of another embodiment of a flexible connection element.

Referring to FIG. 46, the flexible connection element 460 may have an arcuate shaped interface 462 between end portions 464, 466 and intermediate portion or spacer 468. In this embodiment, four coupling members or cords may extend between end members 464, 466. Clamping plates 470 may be provided on each end member adjacent the top and bottom of flange portion 472 to secure, clamp, or affix the cords to the end member.

Figure 47:
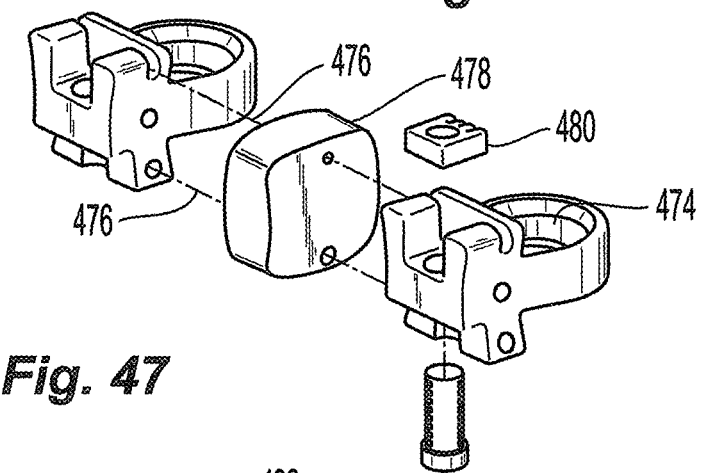
FIG. 47 is an exploded view of another embodiment of a flexible connection element.

Referring to FIG. 47, in a modification of the embodiment shown in FIG. 46, end members 464, 466 may have a laterally positioned opening 474 for side mounting to a post type screw. In this embodiment, an upper and lower coupling member or cord 476 may extend. through intermediate portion 478 and clamping plates 480 may be provided on each end member adjacent the top and bottom of flange portion to secure, clamp or affix cords 476 to the end member.

Figure 48:
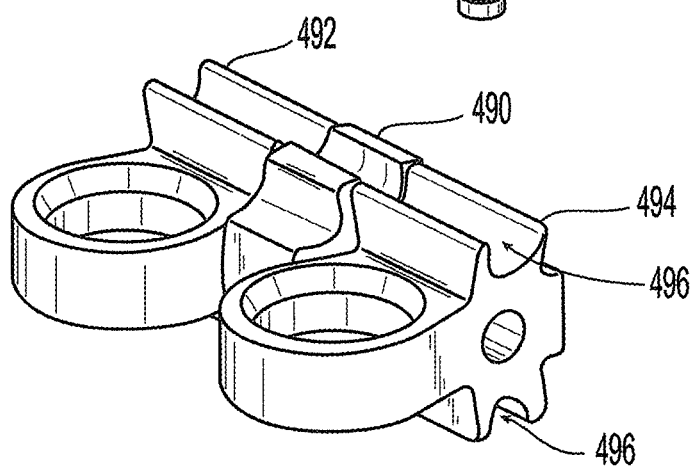
FIG. 48 is a perspective view of another embodiment of a flexible connection element.

Referring to FIG. 48, in a modification of the embodiment shown in FIG. 47, intermediate portion 490 and end members 492, 494 may have a trough, indentation, or groove 496 extending along the top and bottom of the construct and may be configured and dimensioned to accommodate a coupling member or cord therein.

Figure 49:
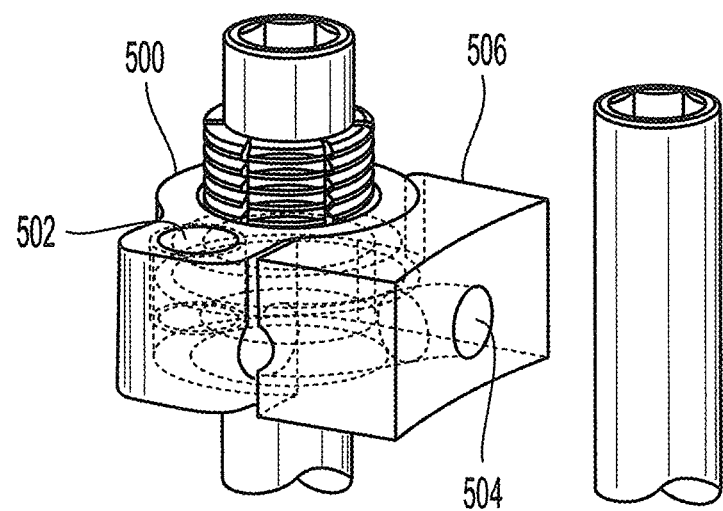
FIG. 49 is a perspective view of another embodiment of a flexible connection element.

Referring to FIG. 49, an alternate side mountable end portion 500 is shown. In this variation, a hole 502 may be provided to accommodate a set screw to secure cord 504 to end member 500. A similar end portion 500 may be provided on an adjacent bone anchor and cord 504 may couple them together with intermediate portion 506 disposed therebetween.

Figure 50:
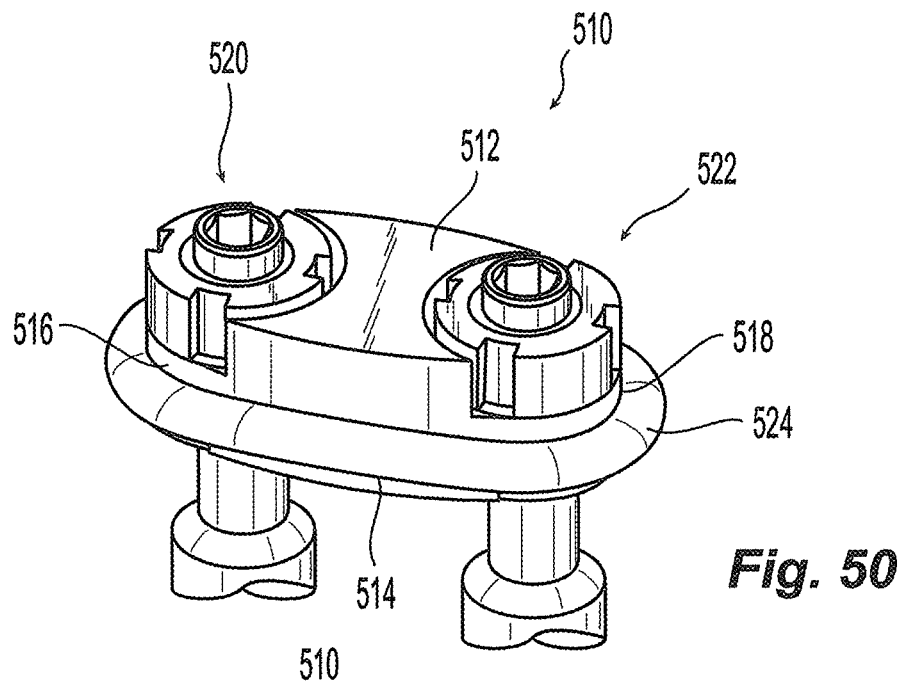
FIGS. 50-52 are perspective views of additional embodiments of flexible connection elements.
Figure 51:
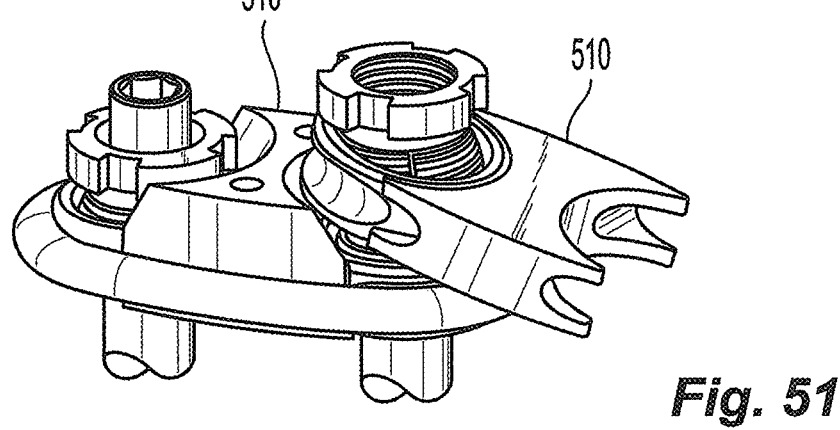

Referring to FIGS. 50-51, an alternate flexible connection element 510 may have an intermediate portion 512 with a generally ovoid or football shape and may have an indentation, groove, or trough 514 extending around the periphery and generally aligned and coextensive with an indentation, groove or trough 516, 518 extending about the periphery of end members 520, 522. When assembled, troughs 514, 516 and 518 extend about the periphery of flexible connection element 510 and are configured and dimensioned to accommodate a coupling member or cord 524 in the shape of a continuous loop. In operation, when end members 520, 522 are compressed together, intermediate portion 512 may be resiliently compressed and/or deformed and when end members are separated, coupling member or cord 524 may be resiliently elastically elongated. As shown in FIG. 51, in one variation the embodiment of FIG. 50 may be used in series with another flexible connection element 510 for spine stabilization over multi levels or motion segments.

Figure 52:
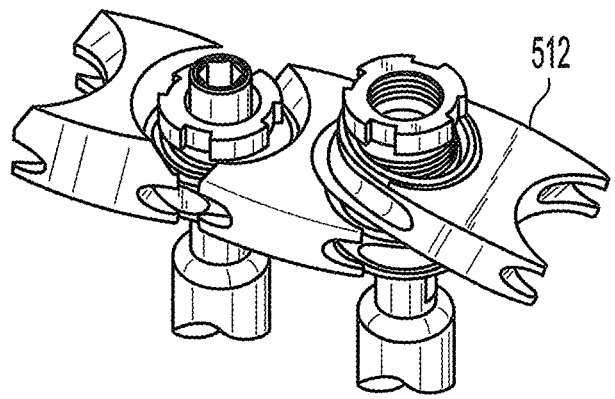

Referring to FIG. 52, in a modification of the embodiment shown in FIG. 50, coupling member or cord 524 may extend internally through intermediate portion 512 and externally around the periphery of end portions 520, 522.

Figure 53:
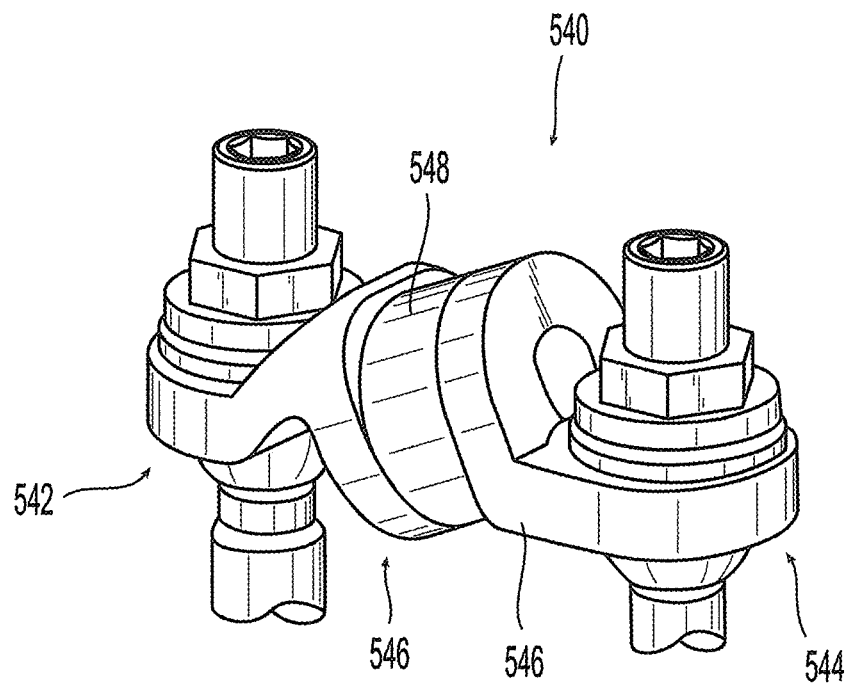
FIGS. 53-54 depict another embodiment of a flexible connection element.
Figure 54:
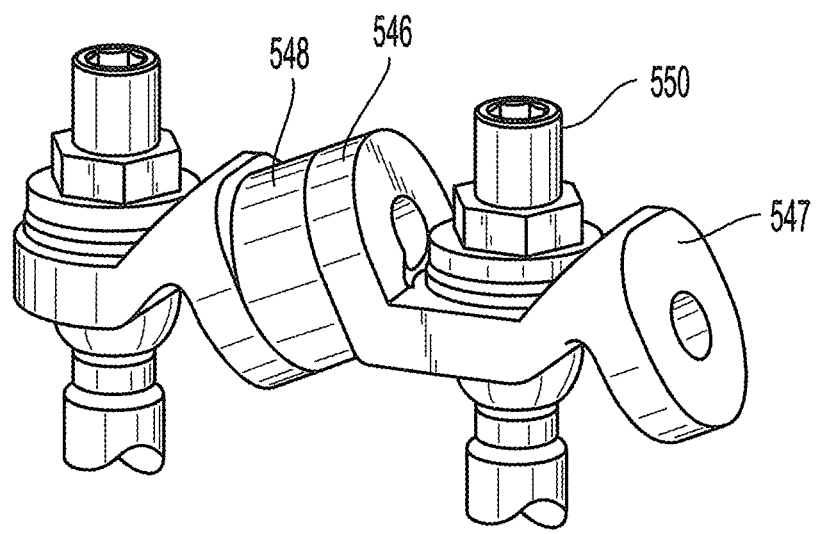

Referring to FIGS. 53-54, in an alternate embodiment of a flexible connection element 540, end members 542, 544 may have an angled end plate or flange 546 to interface with intermediate portion 548. One skilled in the art may appreciate that such an angled flange feature saves space and facilitates installation of flexible connection element 540 in motion segments where space constraints dictate. For example, flexible connection element 540 may be utilized at the L5-S1 level. As shown in FIG. 54, a multilevel construct may be provided with an end portion having angled flange portions 546, 547 on both sides of bone anchor 550 such that flanges 546, 547 may both engage intermediate portions or spacers 548.

Figure 55:
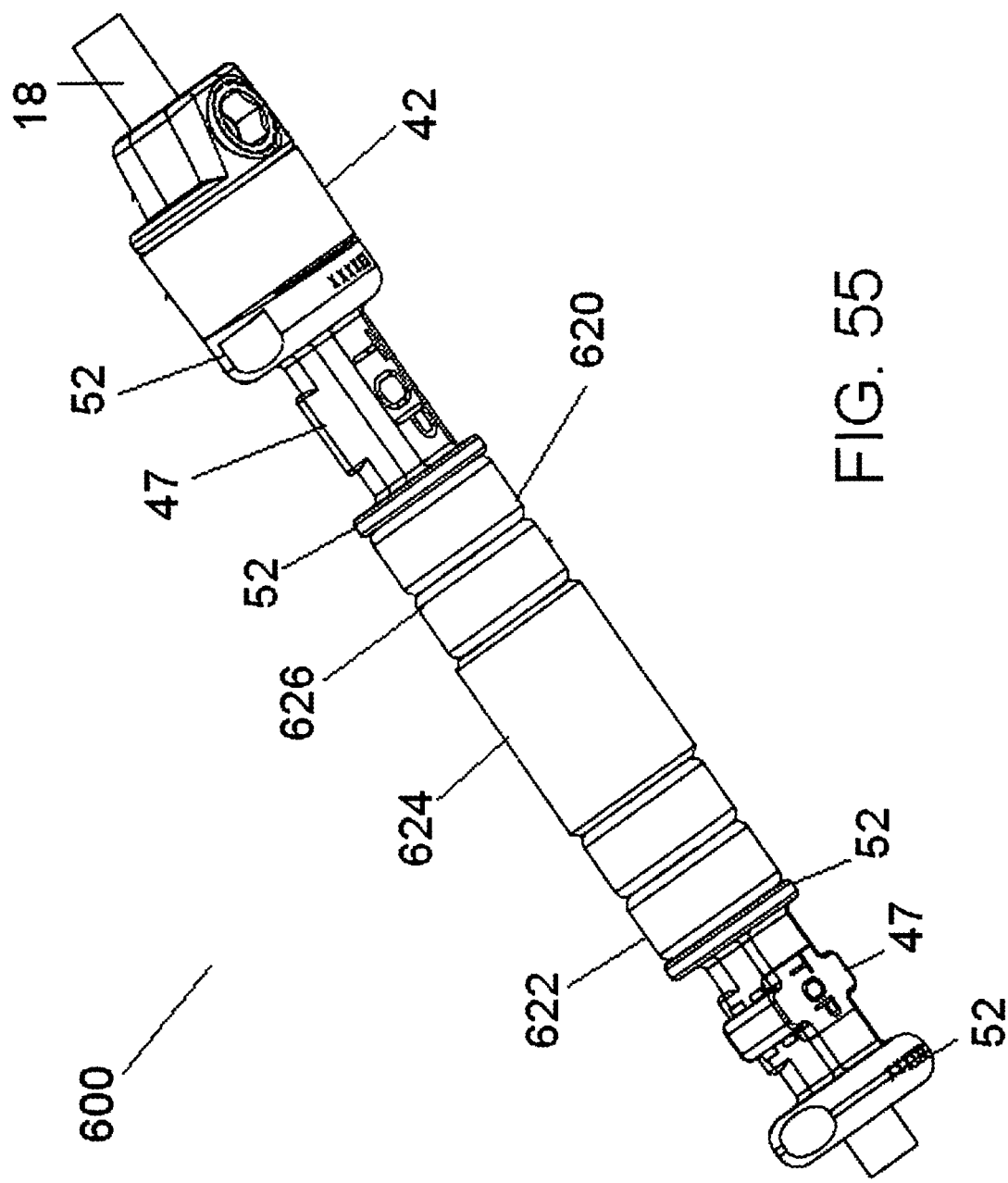
FIG. 55 is a perspective view of another embodiment of a flexible connection assembly including modular rings.

FIG. 55 is a perspective view of another embodiment of a flexible connection assembly including modular rings. The assembly 600 comprises a number of components as in prior embodiments, including one or more spools 47, one or more bumpers 42 positioned adjacent to the one or more spools 47, and a cord 18 that extends therethrough. The one or more spools 47 can include an upper clamp body and a lower clamp body (as shown in FIG. 6), and are capable of being retained by bone fasteners 34 (as shown in FIG. 5). In addition to these components, the assembly 600 comprises one or more modular spacers or rings 620 that are positioned between the spools 47. These modular rings 620 advantageously provide a highly dynamic stabilization system that allows for enhanced motion, physiologic translation and axial compression. Depending on the needs of the patient, a surgeon can apply one or more modular rings 620 to adjust characteristics, such as flexibility and stiffness, of the assembly 600. The modular rings 620 extend around the cord 18 in a similar fashion to the intermediate spacer 16 shown in FIG. 1. However, the modular rings 620 provide even more options for strength and flexibility than the sole intermediate spacer 16, as they can be combined in multiple different ways by a surgeon as desired.

As shown in FIG. 55, the assembly 600 can accommodate one or more modular rings 620 that can be provided by a surgeon depending on the specific needs of a patient. It has been found that modular rings 620 of particular material and shape can provide benefits to the flexible connection assembly. In some embodiments, one or more of the modular rings 620 are formed of PEEK. The advantage of PEEK rings 622 is its biocompatibility. In some embodiments, one or more of the modular rings 620 are formed of polycarbonate-urethane, or PCU. The advantage of PCU rings 624 is that it provides compliance and compressibility. In some embodiments, one or more of the modular rings 620 are formed of a metal or metal alloy, such as titanium or cobalt-chrome (CoCr). The advantage of titanium or CoCr rings 626 is increased strength, with CoCr rings provided even greater strength than titanium if desired.

In the embodiment in FIG. 55, the one or more modular rings 620 are composed of a number of differently sized rings of different materials. For example, the PCU ring 624 is of a length greater than the adjacent PEEK ring 622 and the adjacent titanium ring 626. In addition, in the present embodiment, the one or more modular rings 620 are composed of three different types of materials, including PEEK, PCU and titanium. In the present embodiment, the assembly 600 comprises at least five modular rings, positioned between a pair of spools 47.

FIGS. 56-59 illustrate different embodiments of flexible connection assemblies including different combinations of modular rings 620, in accordance with one or more embodiments. Each of the flexible connection assemblies includes their own advantages, as will be discussed in more detail below.

Figure 56:
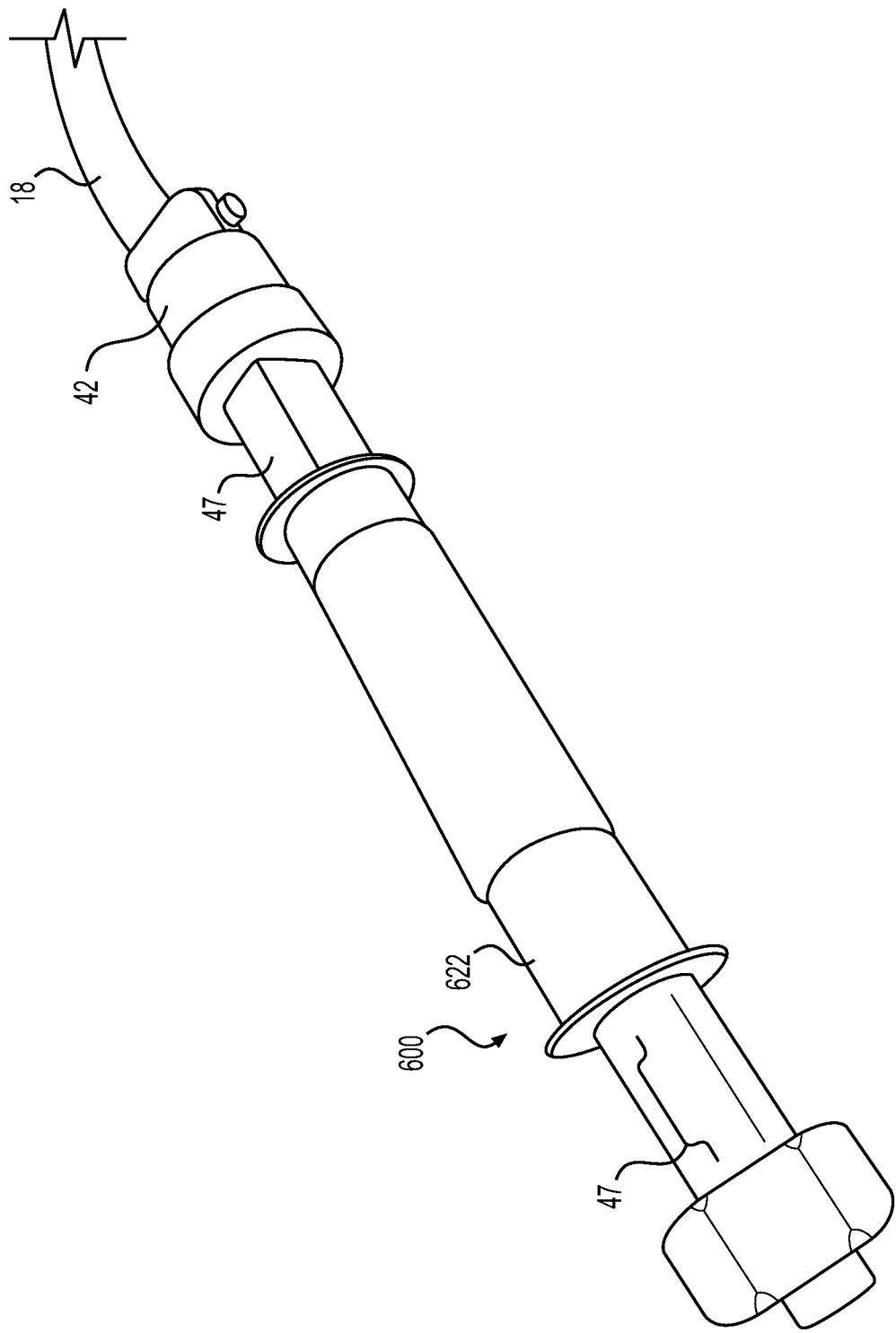
FIG. 56 is a perspective view of a flexible connection assembly including just PEEK rings.

FIG. 56 is a perspective view of a flexible connection assembly including just PEEK rings. The flexible connection assembly 600 comprises a series of PEEK rings 622 stacked adjacent to one another between a pair of spools 47. The PEEK rings 622 advantageously accommodate physiologic movement and translation, such as flexion and extension of the spine. When a patient bends, the PEEK rings 622 advantageously slide and translate over one another, thereby creating a proper bending form.

Figure 57:
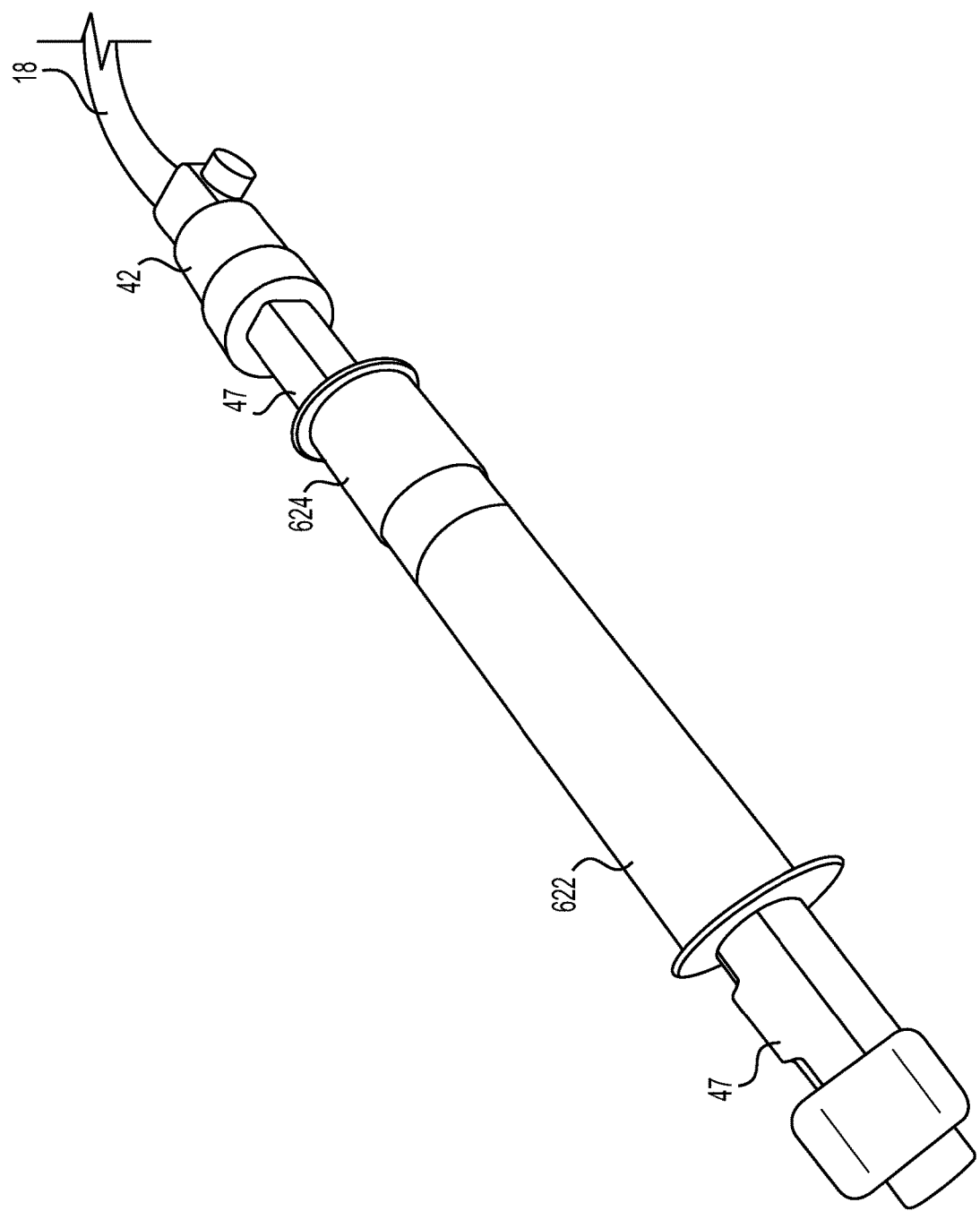
FIG. 57 is a perspective view of a flexible connection assembly including PEEK rings and a PCU ring.

FIG. 57 is a perspective view of a flexible connection assembly including PEEK rings and a PCU ring. The flexible connection assembly 600 comprises a series of PEEK rings 622 stacked adjacent to one another between a pair of spools 47. On one end of the stacked PEEK rings 622 is a PCU ring 624, which advantageously increases the compressibility of the assembly.

Figure 58:
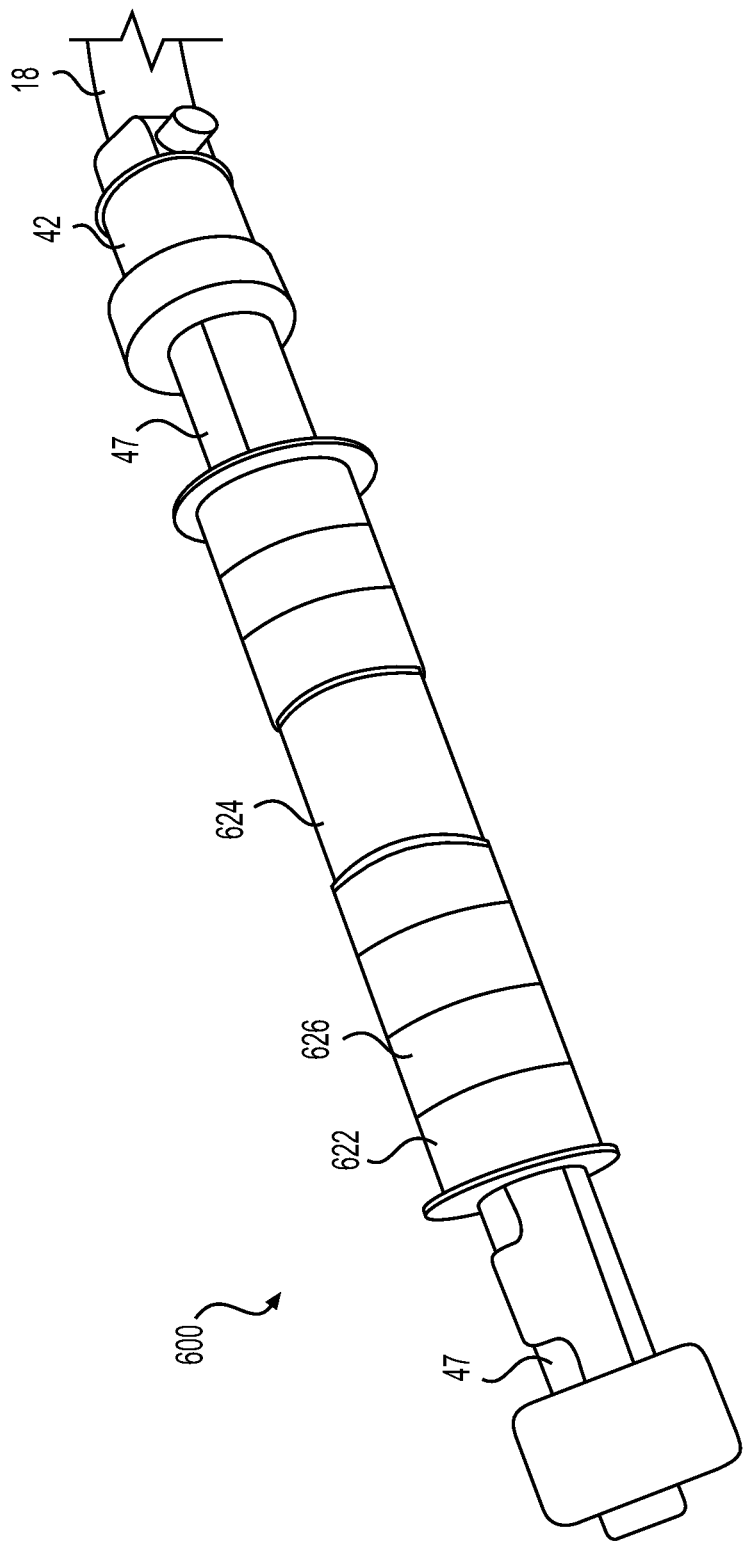
FIG. 58 is a perspective view of a flexible connection assembly including alternating PEEK and metal rings.

FIG. 58 is a perspective view of a flexible connection assembly including alternating PEEK and metal rings. The flexible connection assembly 600 comprises a series of PEEK rings 622 alternating with metal rings 626. By alternating the PEEK and metal rings, this construct advantageously prevents metal on metal contact, thereby reducing the risk of metal shavings in a patient, while still maintaining a construct of high strength. In addition to the PEEK and metal rings, the assembly 600 further comprises a PCU ring 624, which increases the compressiblity of the assembly.

Figure 59:
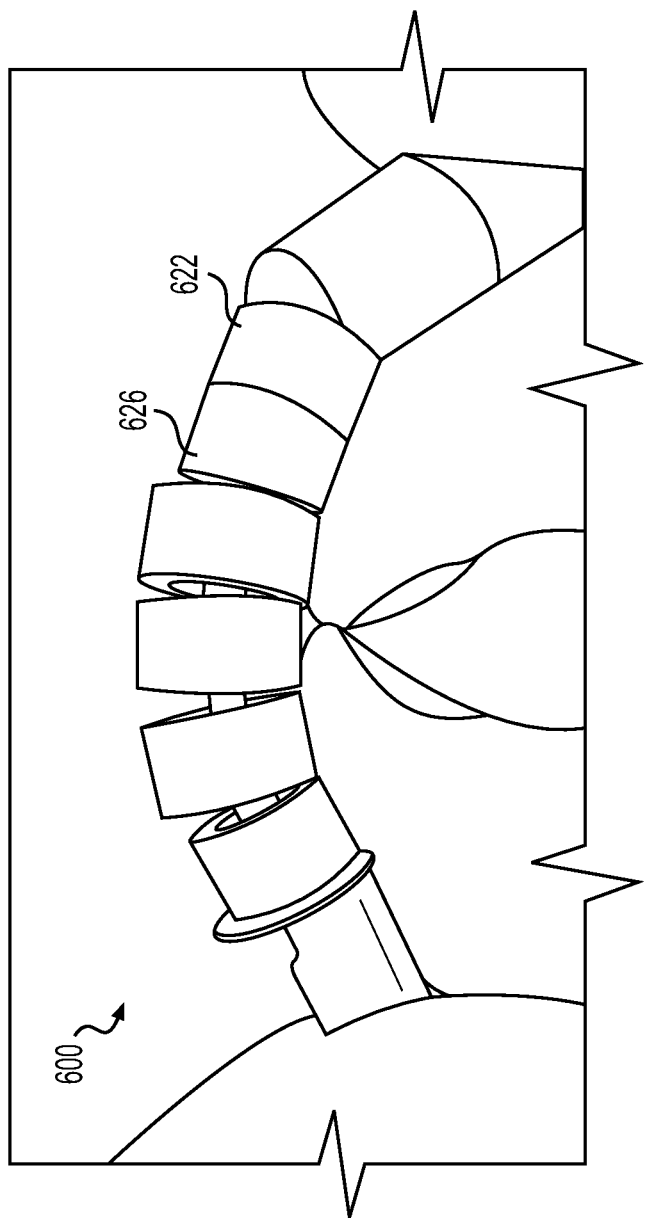
FIG. 59 is a perspective view of the flexible connection assembly of FIG. 58 in a flexed state.

FIG. 59 is a perspective view of a flexible connection assembly having alternating PEEK and metal rings in a flexed state. From this view, one can see how providing a plurality of modular rings increases the ability of the construct to maintain better physiological translation in-line with a patient's movements.

Bone Fasteners

The bone fasteners included in the disclosed system include any type of fastener that may be attached to the flexible connection element of the invention, while remaining securely fastened onto the intended bone. Thus, the bone fasteners may include mono-axial screws, polyaxial screws, post-type screws, helical blades, expandable screws, such as Mollie bolt type fasteners, which are inserted or screwed into the bone and expand by way of some type of expansion mechanism, conventional screws, staples, sublaminar hooks, and the like. In one embodiment, the bone fasteners are coated with any number of suitable osteoinductive or osteoconductive materials to enhance fixation in the bone. In another embodiment, the bone fasteners are fenestrated to enhance bony ingrowth or to further anchor the fastener to the bone.

The bone fasteners may be made from a host of materials. For example, the fasteners may be formed from natural/biological materials, such as allograft, xenograft, and cortical bone. The fasteners may also be formed from synthetic bioresorbable materials, such as polyanhydride, polyactide, polyglycolide, polyorthoester, polyphosphazene, calcium phosphate, hydroxyapatite, bioactive glass, tyrosine-derived polycarbonate, and mixtures thereof. In another embodiment, the fasteners are formed from non-bioresorbable materials including, but not limited to, stainless steel, titanium, titanium alloys, cobalt chrome alloys, shape-memory alloys, and carbon-reinforced polymer composites.

In addition, the fasteners may include growth factors for bone ingrowth and bony attachment, or for soft tissue ingrowth. Non-limiting examples of growth factors include insulin-like growth factor 1, basic fibroblast growth factor, transforming growth factor 13-1, platelet-derived growth factor, bone-derived growth factors, arginine, bone morphogenetic protein, LIM mineralization protein, and combinations thereof As mentioned previously, the flexible connection element also may be used in other component of a spinal fixation system. For instance, it may be used as part of a transconnector. In this embodiment, the flexible connection element may be disposed between two fasteners connected to rods positioned along the length of the spine. Any fastener that may be suitable for a conventional transconnector may be used with the present invention. Some examples of fasteners are described in U.S. Pat. No. 6,565,565 to Yuan, U.S. Pat. No. 6,562,040 to Wagner, U.S. Pat. No. 6,551,318 to Stahurski, and U.S. Pat. No. 6,540,749 to Schafer, all of which are incorporated herein in their entireties.

Assembly of the Systems

The flexible connection element may be connected to fasteners in a number of ways, i.e., so that the connection is constrained, unconstrained, articulated, or combinations thereof. For example, the end portions may be attached to bone anchors and inserted or installed adjacent a motion segment of the spine. The flexible connection element may be inserted into or onto anchor heads, which can be side-loading or top-loading in this aspect of the invention. Following the placement of the flexible connection element upon the anchor heads, clamping screws may be inserted into or upon the anchor heads and firmly screwed down securing all the connected elements in place. This design would generally allow flexibility between the two bone fasteners.

The stiffness of the disclosed systems may also be adjusted during the operation and post-operation using a set screw. This would allow surgeons and doctors to make adjustments depending on a specific scenario.

The system, once assembled, may serve a variety of functions in the motion segment unit. For example, the system may reduce the load on the degenerative disc and/or facet joints in the motion segment unit. In addition, the height of the adjacent vertebrae may be restored to eliminate crushing or slipping of the disc therebetween. Moreover, lordosis may be created/preserved using the disclosed systems in at least one motion segment unit of the spine. Furthermore, the stiffness of the motion segment unit may be restored with the implementation of the system of the invention.

In some embodiments, flexible connection elements may be disposed in combination with rods used to make a portion of the system rigid. For example, a motion segment neighboring a treated area that has been essentially immobilized with a rigid stabilization system may be supported with a flexible connection element.

While it is apparent that the invention disclosed herein is well calculated to fulfill the objects stated above, it will be appreciated that numerous modifications and embodiments may be devised by those skilled in the art.

What is claimed is:

1. A spine stabilization system comprising:
a first spool having an upper clamp body and a lower clamp body, wherein the upper clamp body comprises a pair of downwardly extending arms, and each of the arms of the upper clamp body overlie an outer surface of the lower clamp body;
a second spool;
a first receiver for receiving the first spool;
a second receiver for receiving the second spool;
a plurality of modular rings that extend between the first spool and the second spool;
at least one polycarbonate-urethane (PCU) ring disposed between two of the plurality of modular rings, wherein the at least one PCU ring is greater in length than each of the plurality of modular rings;
a flexible cord that extends through the first spool, second spool and the plurality of modular rings; and
a resiliently compressible member disposed over the cord and positioned adjacent an outer endplate of the first spool or an outer endplate of the second spool; and
an end portion positioned adjacent to the resiliently compressible member, and a portion of the end portion extends into an opening in the resiliently compressible member.

2. The system of claim 1, wherein the first receiver comprises a portion of a pedicle screw.

3. The system of claim 1, further comprising at least two modular rings in contact with one another and positioned between the first and second spools.

4. The system of claim 3, wherein at least modular one ring is formed of a metal and another modular ring is formed of a polymer.

5. The system of claim 3, wherein the plurality of modular rings comprise alternating PEEK and metal rings.

6. The system of claim 1, wherein the first spool comprises a middle body portion and a pair of flanges.

7. The system of claim 1, wherein at least one of the first spool and the second spool is slidable relative to the flexible cord.

8. The system of claim 1, wherein the resiliently compressible member is a bumper.

9. A spine stabilization system comprising:
a first endplate including a first spool having an upper clamp body and a lower clamp body, wherein the upper clamp body comprises a pair of downwardly extending arms, and each of the arms of the upper clamp body overlie an outer surface of the lower clamp body;
a second endplate including a second spool;
a plurality of modular rings that extend between the first endplate and the second endplate;

at least one polycarbonate-urethane (PCU) ring disposed between two of the plurality of modular rings, wherein the at least one PCU ring is greater in length than each of the plurality of rings;

a flexible cord that extends through the first endplate, second endplate and the plurality of modular rings; and a resiliently compressible member disposed over the cord and positioned adjacent an outer endplate of the first spool or an outer endplate of the second spool; and an end portion positioned adjacent to the resiliently compressible member, and a portion of the end portion extends into an opening in the resiliently compressible member.

10. The system of claim 9, further comprising a first receiver for receiving the first spool.

11. The system of claim 10, wherein the receiver comprises a pedicle screw.

12. The system of claim 11, wherein the plurality of modular rings comprise at least four rings.

13. The system of claim 12, wherein the at least four rings comprise alternating rings of PEEK and metal.

14. The system of claim 12, wherein the at least four rings are stacked adjacent to one another.

15. The system of claim 12, wherein the at least four rings comprise all PEEK.

16. The system of claim 12, wherein the lower clamp body includes a protrusion configured to engage one of the arms of the upper clamp body.

17. The system of claim 9, wherein the lower clamp body includes two protrusions on each side of the middle body portion, which are configured to engage each of the arms of the upper clamp body, respectively.

18. The system of claim 17, wherein at least one of the protrusions includes a chamfer or angled surface to facilitate arm deflection.

19. The system of claim 1, wherein the end portion includes a shoulder portion and a flange extending outwardly from the shoulder portion, and the shoulder portion is received in the resiliently compressible member.

* * * * *